United States Patent
Liebeschuetz et al.

(10) Patent No.: US 6,262,069 B1
(45) Date of Patent: Jul. 17, 2001

(54) 1-AMINO-7-ISOQUINOLINE DERIVATIVES AS SERINE PROTEASE INHIBITORS

(75) Inventors: John Walter Liebeschuetz, Bollington; William Alexander Wylie, Stockport; Bohdan Waszkowycz, Wilmslow; Christopher William Murray, Macclesfield; Andrew David Rimmer, Chorley; Pauline Mary Welsh, Macclesfield; Stuart Donald Jones, Prestbury; Jonathan Michael Ernest Roscoe, Holsworthy; Stephan Clinton Young, Stockport; Phillip John Morgan, Congleton; Nicholas Paul Camp, Macclesfield; Andrew Philip Austin Crew, Congleton, all of (GB)

(73) Assignee: Protherics Molecular Design Limited, Macclesfield (GB)

( * ) Notice: Subject to any disclaimer, the term of this patent is extended or adjusted under 35 U.S.C. 154(b) by 0 days.

(21) Appl. No.: 09/485,677

(22) PCT Filed: Aug. 28, 1998

(86) PCT No.: PCT/GB98/02600
§ 371 Date: Feb. 25, 2000
§ 102(e) Date: Feb. 25, 2000

(87) PCT Pub. No.: WO99/11657
PCT Pub. Date: Mar. 11, 1999

(30) Foreign Application Priority Data

Aug. 29, 1997 (GB) .................................................. 9718392
Feb. 13, 1998 (GB) .................................................. 9803173

(51) Int. Cl.$^7$ ........................ A61K 31/47; C27D 217/22
(52) U.S. Cl. ............................................ 514/310; 546/143
(58) Field of Search ............................ 546/143; 514/310

(56) References Cited

U.S. PATENT DOCUMENTS 5,346,907  9/1994  Kerwin et al. .
5,455,348  10/1995  Austel et al. .................. 544/238
5,519,036  5/1996  Himmelsbach et al. ............. 514/310
5,731,315  3/1998  Ewing et al. .................. 514/269
6,063,789  5/2000  Hamley .

FOREIGN PATENT DOCUMENTS

WO 91/00725  1/1991  (WO) .
WO98/25611  6/1998  (WO) .

OTHER PUBLICATIONS

CA 129:81744, abstract of Choi–Sledeski, WO 9825611, 1998.

Primary Examiner—D. Margaret Seaman
(74) Attorney, Agent, or Firm—Martin A. Hay

(57) ABSTRACT

The invention relates to serine protease inhibitor compounds of fornula (I) where $R_1$ is hydrogen, halo, cyano, nitro or hydroxyl, amino, alkoxy, alkyl amminoalkyl, hydroxyalkyl, thiol, alkylthio, aminosulphonyl alkoxyalkyl, alkoxycarbonyl, acyloxymethoxycabonyl or alkylamino optionally substituted by hydroxy, alkylamino, alkoxy, oxo, aryl, cycloalkyl, amino, halo, cyano, nitro, thiol, alkylthio, alkylsulphonyl, alkylsulphenyl, alkylsulphonamido, alkylaminosulphonyl, haloalkoxy and haloalkyl; $R_2$ is hydrogen, halo, methyl amino, hydroxy, or oxo; and R is X—X—Y($R_7$)—L—Lp(D)n; wheren each X independently is a C, N, O or S atom or a CO, $CR_1$, $C(R_1)_2$ or $NR_1$ group, at least one X being C, CO, $CR_1$ or a $C(R_1)_2$ group; Y (the α-atom) is a nitrogen atom or a $CR_1$ group or Y and L taken together form a cyclic group; $R_7$ is a lipophilic group selected from alkyl, alkenyl, mono- or bi-cycloalkyl, aryl, heteroaryl, mono- or bicycloalkylalkyl, mono- or bicycloalkylakenyl, aralkyl, heteroaryl-alkyl, arylalkenyl, heteroarylalkenyl all optionally substituted by a group $R_1$; L is an organic linker group containing 1 to 5 backbone atoms selected from C, N, O and S, or a branched alkyl or cyclic group; Lp is a lipophilic organic group selected from alkyl, heterocyclic, alkenyl, alkaryl cycloalkyl, polycycloalkyl, cycloalkenyl, aryl, aralkyl or haloalkyl group or a combination of two or more such groups optionally substituted by one or more of oxa, thia, aza or $R_1$ groups; D is a hydrogen bond donor group; and n is 0, 1 or 2 and salts thereof.

28 Claims, No Drawings

1-AMINO-7-ISOQUINOLINE DERIVATIVES AS SERINE PROTEASE INHIBITORS

This application is a 371 of PCT/GB98/02600, filed Aug. 28, 1998.

This invention relates to compounds which are inhibitors of serine proteases and to pharmaceutical compositions thereof and their use in the treatment of the human or animal body.

The serine proteases are a group of proteolytic enzymes which have a common catalytic mechanism characterized by a particularly reactive Ser residue. Examples of serine proteases include trypsin, tryptase, chymotrypsin, elastase, thrombin, plasmin, kallikrein, Complement C1, acrosomal protease, lysosomal protease, cocoonase, α-lytic protease, protease A, protease B. serine carboxypeptidase II, subtilisin, urokinase, Factor VIIa, Factor IXa, and Factor Xa. The serine proteases have been investigated extensively over a period of several decades and the therapeutic value of inhibitors of serine proteases is well understood.

Serine protease inhibitors play a central role in the regulation of a wide variety of physiological process including coagulation, fibrinolysis, fertilization, development, malignancy, neuromuscular patterning and inflammation. It is well known that these compounds inhibit a variety of circulating proteases as well as proteases that are activated or released in tissue. It is also becoming clear that serine protease inhibitors inhibit critical cellular processes, such as adhesion, migration, free radical production and apoptosis. In addition, animal experiments indicate that intravenously administered serine protease inhibitors, variants or cells expressing serine protease inhibitors, provide a protective effect against tissue damage.

Serine protease inhibitors have also been predicted to have potential beneficial uses in the treatment of disease in a wide variety of clinical areas such as oncology, neurology, haematology, pulmonary medicine, immunology, inflammation and infectious disease.

In particular serine protease inhibitors may be beneficial in the treatment of thrombotic diseases, asthma, emphysema, cirrhosis, arthritis, carcinoma, melanoma, restenois, atheroma, trauma, shock and reperfusion injury.

Thus for example an inhibitor of Factor Xa has value as a therapeutic agent as an anticoagulant, e.g. in the treatment and prevention of thrombotic disorders. The use of a Factor Xa inhibitor as an anticoagulant is desirable in view of the selectivity of its effect. Many clinically approved anticoagulants have been associated with adverse events owing to the non-specific nature of their effects on the coagulation cascade.

Also, there are well-known associations of α1 protease inhibitor deficiency with emphysema and cirrhosis and C1 esterase inhibitor deficiency with angioedema.

We have now found that certain novel amino substituted fused bicyclic compounds are particularly effective as inhibitors of serine proteases, especially proteases with negatively charged P1 specificity pockets, and most especially the serine proteases thrombin, trypsin, urokinase and Factor Xa. It is envisaged that compounds of the type described below will be readily bioavailable, particularly orally bioavailable.

Thus viewed from one aspect the invention provides serine protease inhibitor compounds of formula I

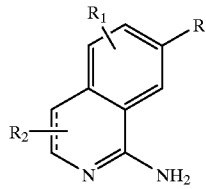

(I)

(where $R_1$ is hydrogen, halo, cyano, nitro or hydroxyl, amino, alkoxy, alkyl, aminoalkyl, hydroxyalkyl, thiol, alkylthio, aminosulphonyl, alkoxyalkyl, alkoxycarbonyl, acyloxymethoxycarbonyl or alkylamino optionally substituted by hydroxy, alkylamino, alkoxy, oxo, aryl, cycloalkyl, amino, halo, cyano, nitro, thiol, alkylthio, alkylsulphonyl, alkylsulphenyl, alkylsulphonamido, alkylaminosulphonyl, haloalkoxy and haloalkyl;

$R_2$ is hydrogen, halo, methyl, amino, hydroxy or oxo; and

R is X—X—Y($R_7$)—L—Lp(D)n (wherein each X independently is a C, N, O or S atom or a CO, $CR_1$, $C(R_1)_2$ or $NR_1$ group, at least one X being C, CO, $CR_1$ or a $C(R_1)_2$ group;

Y (the α-atom) is a nitrogen atom or a $CR_1$ group or Y and L taken together form a cyclic group;

$R_7$ is a lipophilic group, e.g. alkyl, alkenyl, mono- or bi-cycloalkyl, aryl, heteroaryl, mono- or bicycloalkylalkyl, mono- or bicycloalkylalkenyl, aralkyl, heteroaryl-alkyl, arylalkenyl, heteroarylalkenyl all optionally substituted by a group $R_1$;

L is an organic linker group containing 1 to 5 backbone atoms selected from C, N, O and S, or a branched alkyl or cyclic group;

Lp is a lipophilic organic group, e.g. an alkyl, heterocyclic, alkenyl, alkaryl, cycloalkyl, polycycloalkyl, cycloalkenyl, aryl, aralkyl or haloalkyl group or a combination of two or more such groups optionally substituted by one or more of oxa, thia, aza or $R_1$ groups, preferably a group containing up to 25 carbon atoms;

D is a hydrogen bond donor group; and n is 0, 1 or 2);

or a physiologically tolerable salt thereof, e.g. a halide, phosphate or sulphate salt or a salt with ammonium or an organic amine such as ethylamine or meglumine.

In the compounds of the invention, unless otherwise indicated, aryl groups preferably contain 5 to 10 ring atoms optionally including 1, 2 or 3 heteroatoms selected from O, N and S; alkyl, alkenyl or alkynyl groups or alkylene moieties preferably contain up to 6 carbons; cyclic groups preferably have ring sizes of 3 to 8 atoms; and fused multicyclic groups preferably contain 8 to 16 ring atoms.

In the compounds of the invention the fused ring system is preferably a 1-aminoisoquinoline system.

Particularly as a substituent on the isoquinoline ring, $R_1$ is preferably hydrogen, hydroxy, amino or alkyl. $R_2$ is preferably hydrogen. Two or more non-hydrogen $R_1$ (or $R_2$) groups may be present on the carbocyclic (or heterocyclic) rings; however a single non-hydrogen $R_1$ (or $R_2$) group is preferred. $R_1$ is preferably on the 6-position of the fused ring system.

R is depicted in formula (I) as being present on the 7-position of the fused ring system although it is also envisaged that the lipophilic group could be present on the 6-position. However, preferably the lipophilic group will be present on the 7-position of the ring.

In the compounds of the invention, where the alpha atom (Y) is carbon it preferably has the conformation that would result from construction from a D-α-aminoacid $NH_2$—$CR_1(R_7)$—COOH. Likewise the fourth substituent $R_1$ at an alpha carbon is preferably a methyl or hydroxymethyl group or most preferably hydrogen.

The linker group X—X from the fused bicyclic group to the alpha atom is preferably selected from —CH=CH—, —CONH—, —$CONR_1$—, —NH—CO—, —NH—$CH_2$, —$CH_2NH$—, —$CH_2O$—, —$OCH_2$—, —COO—, —OC=O— and —$CH_2CHR_1$— (e.g. —$CH_2CH_2$—). Preferably, the X moiety nearest to the alpha atom is an NH or O atom, most preferably a NH group. The X moiety alpha to the fused ring system is preferably a carbon based group such as $CH_2$ or CO, preferably CO. 1-amino-7-carbonylisoquinoline compounds optionally saturated between the 3 and 4 positions are novel and themselves form a further aspect of the invention. 1-amino-7-substituted isoquinoline compounds optionally saturated between the 3 and 4 positions also form an aspect of the invention.

$R_7$ preferably represents an unsubstituted or $R_1$ substituted aryl or cyclohexyl group, preferably phenyl or naphthyl.

The linker group from the alpha atom to the lipophilic group is preferably CO, $CH_2NH$, $CONR_1(CH_2)_m$, $(CH_2)_m$ $(R_1)CO(CH_2)_m$, $(CH_2)_{m+2}$, $(CH_2)_m CO(CH_2)_m$, $(CH_2)_m OC=O$, $(CH_2)_m O$ or $CH=CH(CH_2)_m$ (where each m is independently 0 or 1). The linker may be optionally branched, for example, to incorporate a polar functionality. In one embodiment Y and L taken together form a cyclic group and the alpha atom is therefore a carbon atom. The cyclic group can be unsubstituted or substituted and can have a ring size of from 3 to 8 atoms. Preferably, the cyclic group is a cyclic amide, most preferably wherein the amide nitrogen of the cyclic amide group is bound to the lipophilic group.

The lipophilic group preferably comprises a cycloalkyl, azacycloalkyl, diazacycloalkyl, phenyl, naphthyl, adamantyl, decalinyl, tetrahydrodecalinyl, bicycloalkyl, mono- or diazabicycloalkyl, mono- or bicyclo heteroaromatic or a linear or branched alkyl, alkylene, alkenyl or alkenylene group all optionally substituted by oxa, aza, thia or one or more groups $R_1$, or a combination of at least two such groups linked by a spiro linkage or a single or double bond or by C=O, O, S, SO, $S_2$, $CONR_1$, $NR_1$—CO—, $NR_1$ linkage. For example, representative lipophilic groups include methylcyclohexyl, methylcyclohexylmethyl, methylphenylmethyl, phenylethyl, benzylpiperidinyl, benzoylpiperidinyl, bispiperidinyl or phenylpiperazinyl.

Most preferably, the lipophilic group is selected from

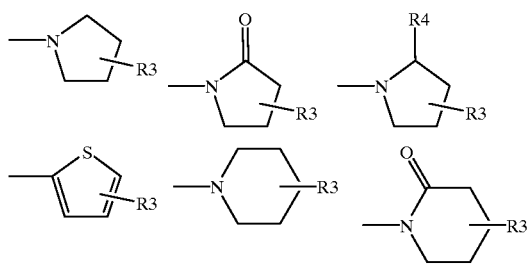

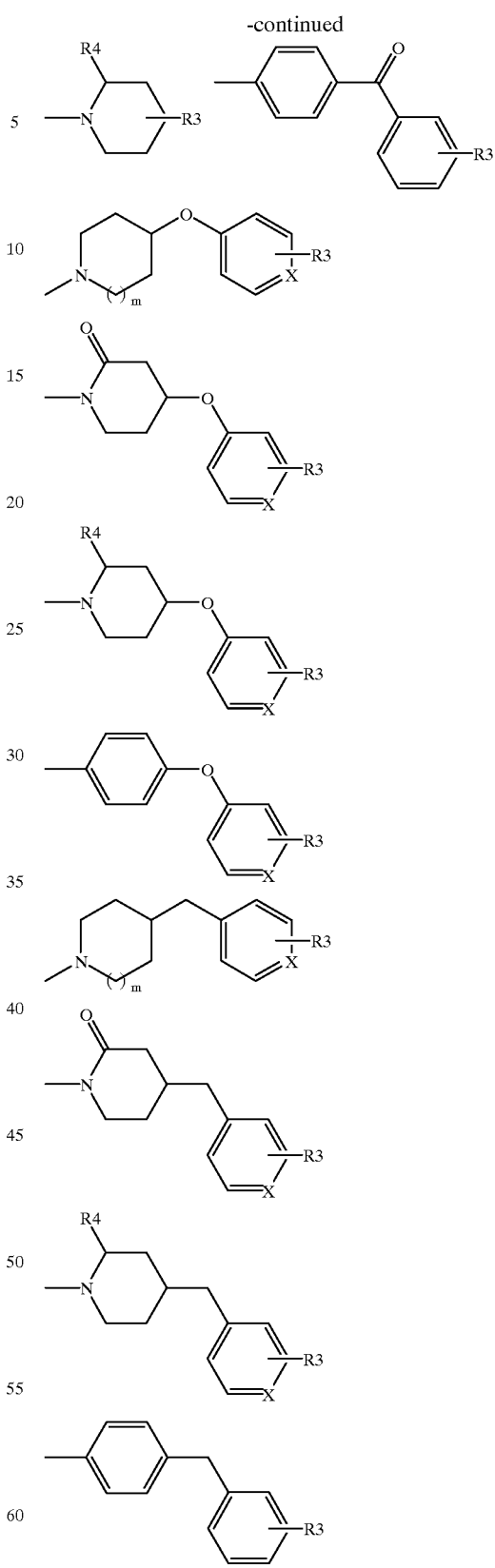

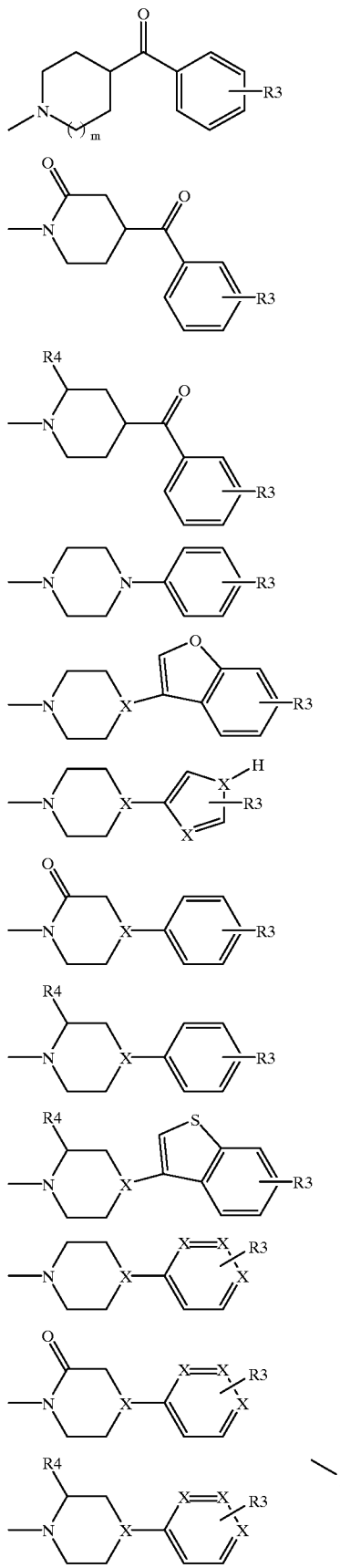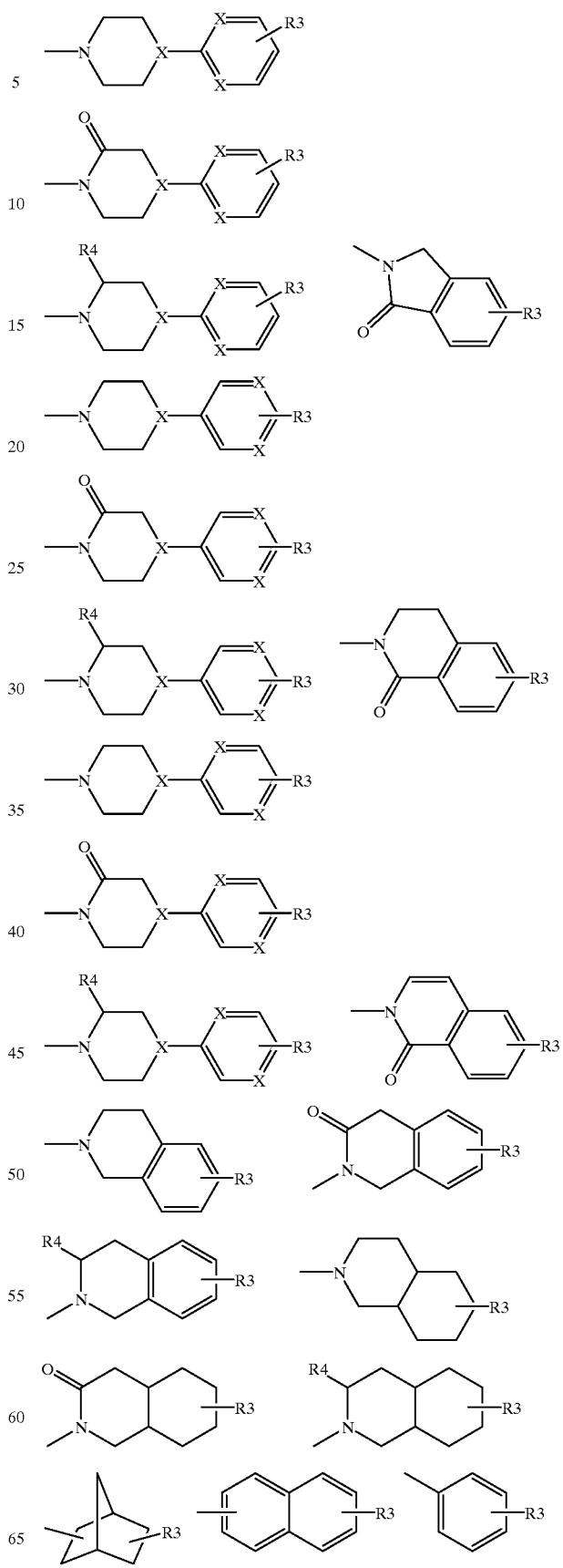

-continued

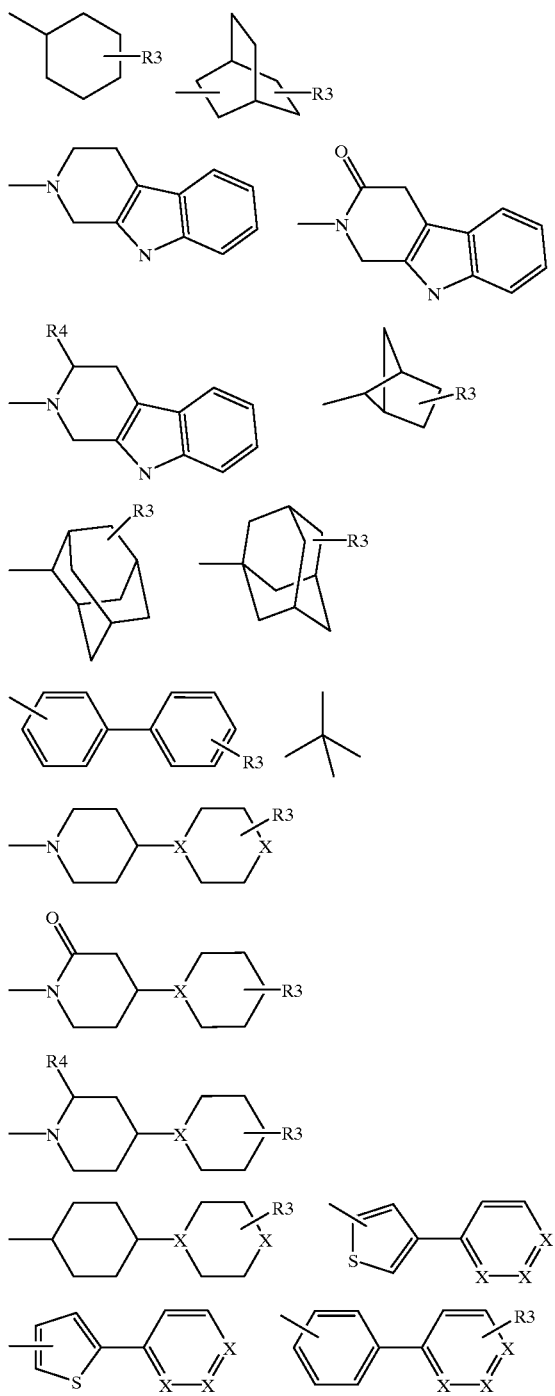

wherein R₃ is R₁, aryl or cycloalkyl;

m represents 0 or 1;

R₄ represents hydrogen, $(CH_2)_w COOH$, $(CH2)_w CON(R_1)_2$, $(CH_2)_w CON\alpha$-AminoAcid;

w represents an integer from 0 to 4; and

X represents CH or N.

For example specific lipophilic groups include

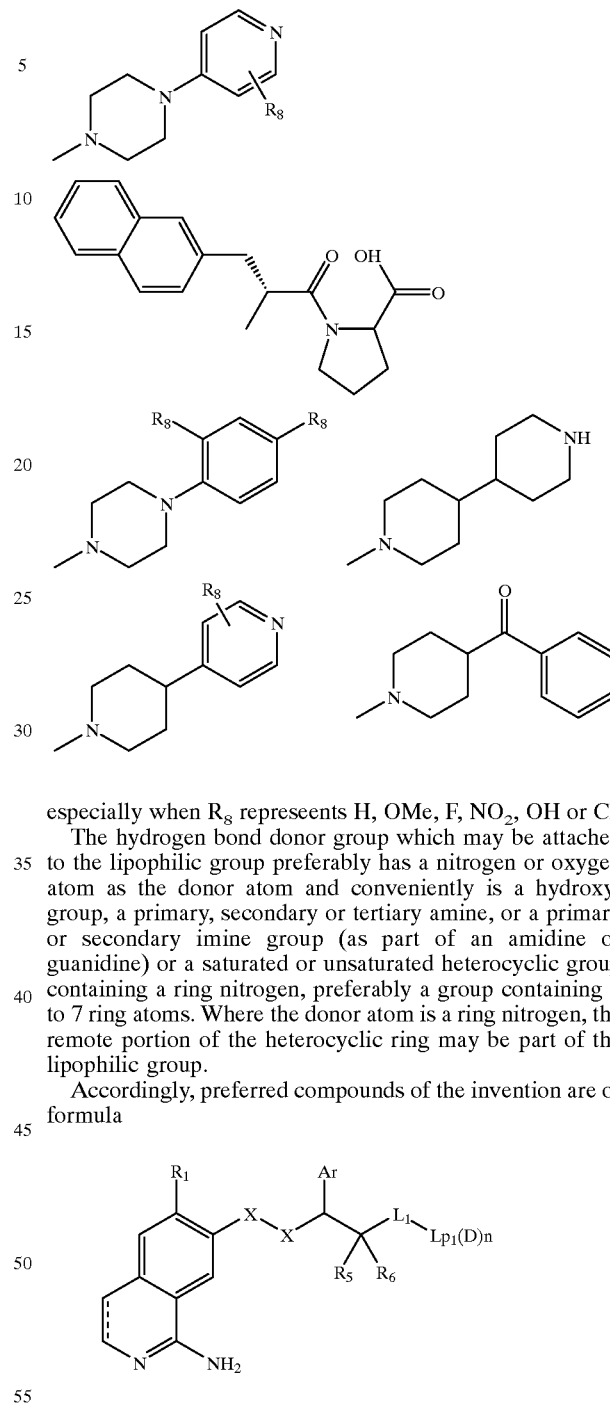

especially when R₈ represents H, OMe, F, NO₂, OH or Cl.

The hydrogen bond donor group which may be attached to the lipophilic group preferably has a nitrogen or oxygen atom as the donor atom and conveniently is a hydroxyl group, a primary, secondary or tertiary amine, or a primary or secondary imine group (as part of an amidine or guanidine) or a saturated or unsaturated heterocyclic group containing a ring nitrogen, preferably a group containing 5 to 7 ring atoms. Where the donor atom is a ring nitrogen, the remote portion of the heterocyclic ring may be part of the lipophilic group.

Accordingly, preferred compounds of the invention are of formula

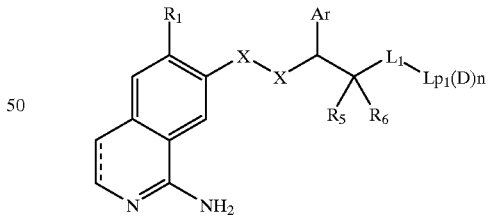

(wherein R₁ is as hereinbefore defined, R₁ preferably being hydrogen, hydroxy or amino);

R₅ and R₆ are hydrogen or taken together with the carbon atom to which they are attached represent a carbonyl group;

Ar is an unsubstituted or R₁ substituted aryl or cyclohexyl group, preferably phenyl or naphthyl;

X—X is —CONH—, —CH₂CH₂—, CH₂O—, —COO—, —CH₂NH—, —OCH₂— or —NHCH₂—;

L₁ is a valence bond or an organic linker group containing 1 to 4 backbone atoms selected from C, N and O;

Lp$_1$ is a cycloalkyl, azacycloalkyl, diazacycloalkyl, phenyl, naphthyl, adamantyl, decalinyl, tetrahydrodecalinyl, bicycloalkyl, mono- or diazabicycloalkyl, mono- or bicyclo heteroaromatic or a linear or branched alkyl, alkylene, alkenyl or alkenylene group all optionally substituted by oxa, aza, thia or a group R$_1$, or a combination of at least two such groups linked by a spiro linkage or a single or double bond or by C=O, O, S, SO, SO$_2$, CONR$_1$, NR$_1$—CO—, NR$_1$ linkage. For example, representative lipophilic groups include a methyl-cyclohexyl, methylcyclohexylmethyl, methylphenylmethyl, phenylethyl, benzylpiperidinyl, benzoylpiperidinyl, bispiperidinyl or phenylpiperazinyl and those as hereinbefore described;

D is a hydrogen bond donor group;

and n is 0, 1 or 2).

In one embodiment, L$_1$ comprises the backbone of an alpha amino acid, the lipophilic group being the side chain of the amino acid. The carboxyl part of the alpha amino acid may be optionally coupled via an amide bond to an amino acid or to a primary or secondary cyclic or acyclic alkyl amine or diamine or via an ester bond to primary or secondary alcohols.

In a preferred embodiment, L$_1$ represents a valence bond and the lipophilic group is bound directly to the carbonyl alpha to the alpha atom via a nitrogen atom which forms part of the lipophilic group. Suitable lipophilic groups in this case therefore include piperidinyl, pyrrolidinyl and piperazinyl. In a preferred embodiment the piperidine or piperazinyl group is further substituted by a phenyl, benzyl, benzoyl, pyridyl, pyridyloxy, piperidinyl or phenoxy group, optionally substituted by one or more R$_1$ groups. Where the lipophilic group is pyridyl it is envisaged then N-oxide pyridyl compounds will also be effective.

In a further embodiment, the lipophilic group has attached a group of the formula —COOR$_1$, CON(R$_1$)$_2$ or —CONα-aminoacid or ester derivative thereof.

In another embodiment the group binding the alpha carbon atom to the lipophilic group comprises a heterocyclic group. Accordingly, preferred compounds of the invention also include

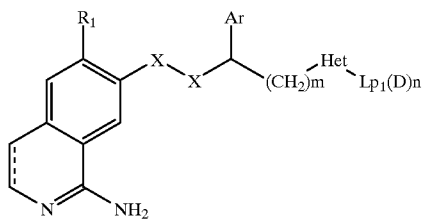

(wherein R$_1$ is as hereinbefore defined R$_1$ preferably being hydrogen, hydroxy or amino);

Ar is an unsubstituted or R$_1$ substituted aryl or cyclohexyl group, preferably phenyl or naphthyl;

X—X is —CONH—, —CH$_2$CH$_2$—, CH$_2$O—, —COO—, —CH$_2$NH—, —OCH$_2$— or —NHCH$_2$—;

m is 0, 1 or 2;

Het is a 5 or 6-membered heterocyclic group interrupted by 1, 2 or 3 heteroatoms selected from O, N and S optionally substituted by a group R$_1$;

Lp$_1$ is a cycloalkyl, azacycloalkyl, diazacycloalkyl, phenyl, naphthyl, adamantyl, decalinyl, tetrahydrodecalinyl, bicycloalkyl, mono- or diazabicycloalkyl, mono- or bicyclo heteroaromatic or a linear or branched alkyl, alkylene, alkenyl or alkenylene group all optionally substituted by a group R$_1$, or a combination of at least two such groups linked by a spiro linkage or a single or double bond or by C=O, O S, SO, SO$_2$, CONR$_1$, NR$_1$—CO—, NR$_1$ linkage; for example representative lipophilic groups include a cyclohexyl, phenyl, benzyl, benzyloxy or benzoyl;

D is a hydrogen bond donor group;

and n is 0, 1 or 2).

Where Het is a five membered ring, the two ring atoms at which it is connected are preferably separated by one ring atom. Where Het is a six-membered ring, the two ring atoms at which it is connected are preferably separated by one or two ring atoms. Representative heterocyclic groups include thiazole, oxazole, oxadiazole, triazole, thiadiazole or imidazole. Where the heterocyclic group is substituted by R$_1$ this is preferably a COOH, CON(R$_1$)$_2$ or COOR$_1$ connected to the heterocycle via a valence bond or alkylene chain.

In a further embodiment, the lipophilic group has attached a group of the formula —COOR$_1$ or —CONα-aminoacid or ester derivative thereof.

Especially preferred compounds according to the invention include 1-Aminoisoquinolin-7-oyl-D-phenylglycinyl-D-2-naphthylalaninylproline, 1-Aminoisoquinolin-7-oyl-D-phenylglycine-4-(4'-pyridyl) piperidinamide, 1-Aminoisoquinolin-7-oyl-D-phenylglycine-4-methoxybenzylamide, 1-Aminoisoquinolin-7-oyl-D-phenylglycine-4-(4'-hydroxyphenyl) piperazinamide, 1-Aminoisoquinolin-7-oyl-D-phenylglycine-4-(2,4-difluorophenyl) piperazinamide, 1-Aminoisoquinolin-7-oyl-D-cyclohexylglycine-4-(4'-pyridyl) piperazinamide, 1-Aminoisoquinolin-7-oyl-D,L-1-naphthylglycine-4,4-bipiperidinamide, 2(R)-{[N-(1-Aminoisoquinoline)-7-oyl] amino}-2-phenylethyl-4-methylbenzamide and 1-Aminoisoquinolin-7-oyl-D-phenylglycine-4,4'-(1'-methyl)bipiperidinamide.

The use of aminoisoquinolines, particularly 1-aminoisoquinolines, more particulary 6 and/or 7 substituted isoquinolines, especially 7-substituted-1,6-diaminoisoquinolines, as serine protease inhibitors, especially factor Xa inhibitors, in particular in therapeutic or prophylactic treatments of humans or non-human animals, particularly mammals, is novel and forms a further aspect of the present invention.

The compounds of the invention may be prepared by conventional chemical synthetic routes, e.g. by amide bond formation to couple the fused bicyclic group to the lipophilic group. A preferred fused bicyclic group for coupling to the lipophilic group is 1-amino-7-carboxyisoquinoline which can be prepared from the readily avaliable starting material 7-carboxyisoquinoline (F. T. Tyson, JACS, 1939,61,183). Amination of the 7-carboxyisoquinoline can be readily effected using ammonia as described in the Examples below.

Preparation of the lipophilic group is conveniently effected from for example LpNH$_2$ (where Lp is as hereinbefore defined). LpNH$_2$ may be attached to a resin to allow routine solid phase peptide synthesis to be carried out. The resin attached LpNH$_2$ moiety can then be coupled by conventional techniques to a suitably protected amino acid, whose side chain will form the R$_1$ group, via for example a free amino group in the Lp group. Deprotection can then be effected before coupling to 1-amino-7-carboxyisoquinoline and isolation from the resin. This method is illustrated in Scheme 1 below.

Alternatively, the synthesis can be initiated from an LpCOOH derivative and the carboxyl functionality can be coupled to the resin. Conventional peptide synthesis as illustrated in Scheme 2 can then be carried out.

Further peptide based syntheses are illustrated in Schemes 3 to 5.
Scheme 1
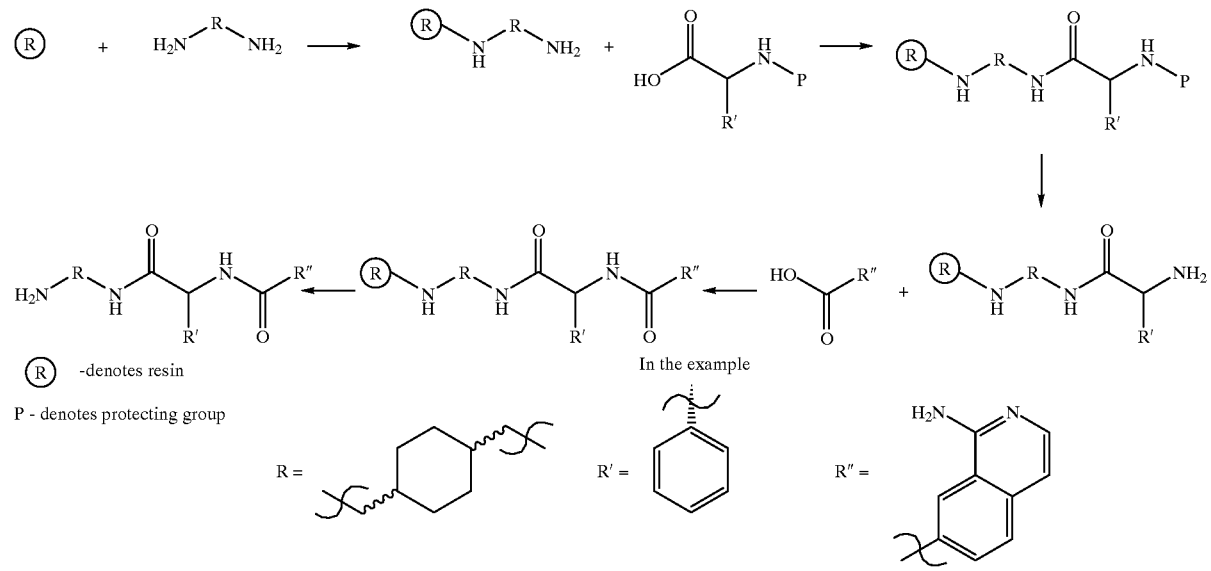
Scheme 2
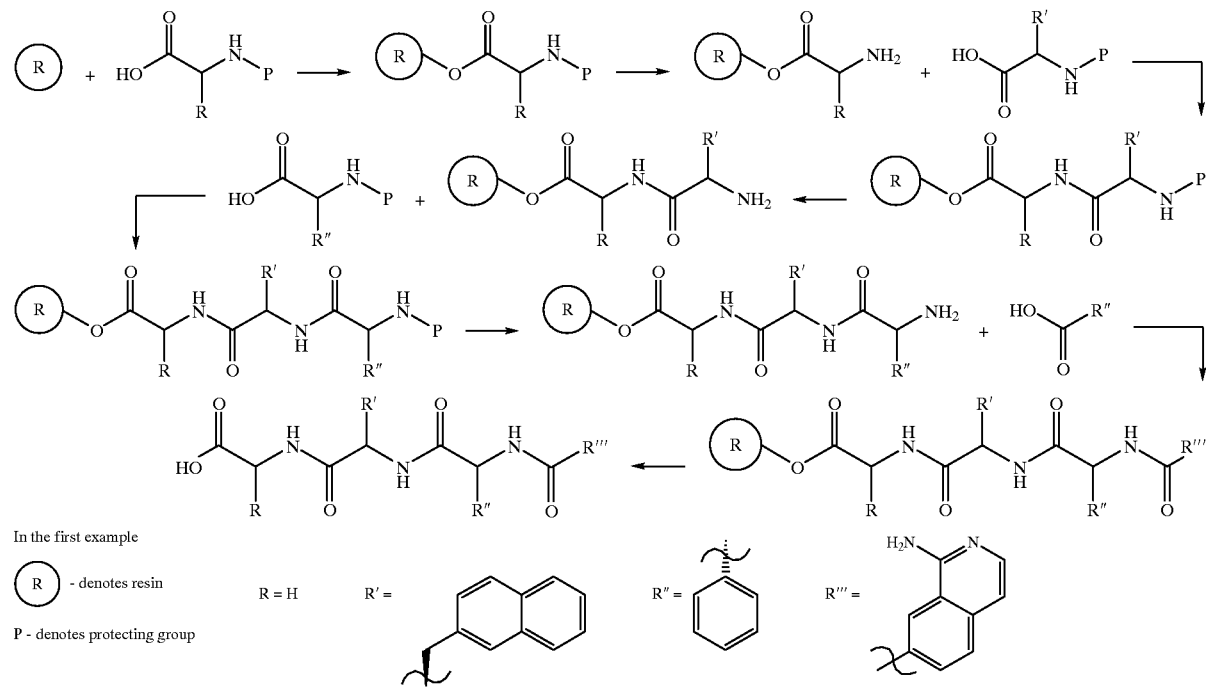

Scheme 3
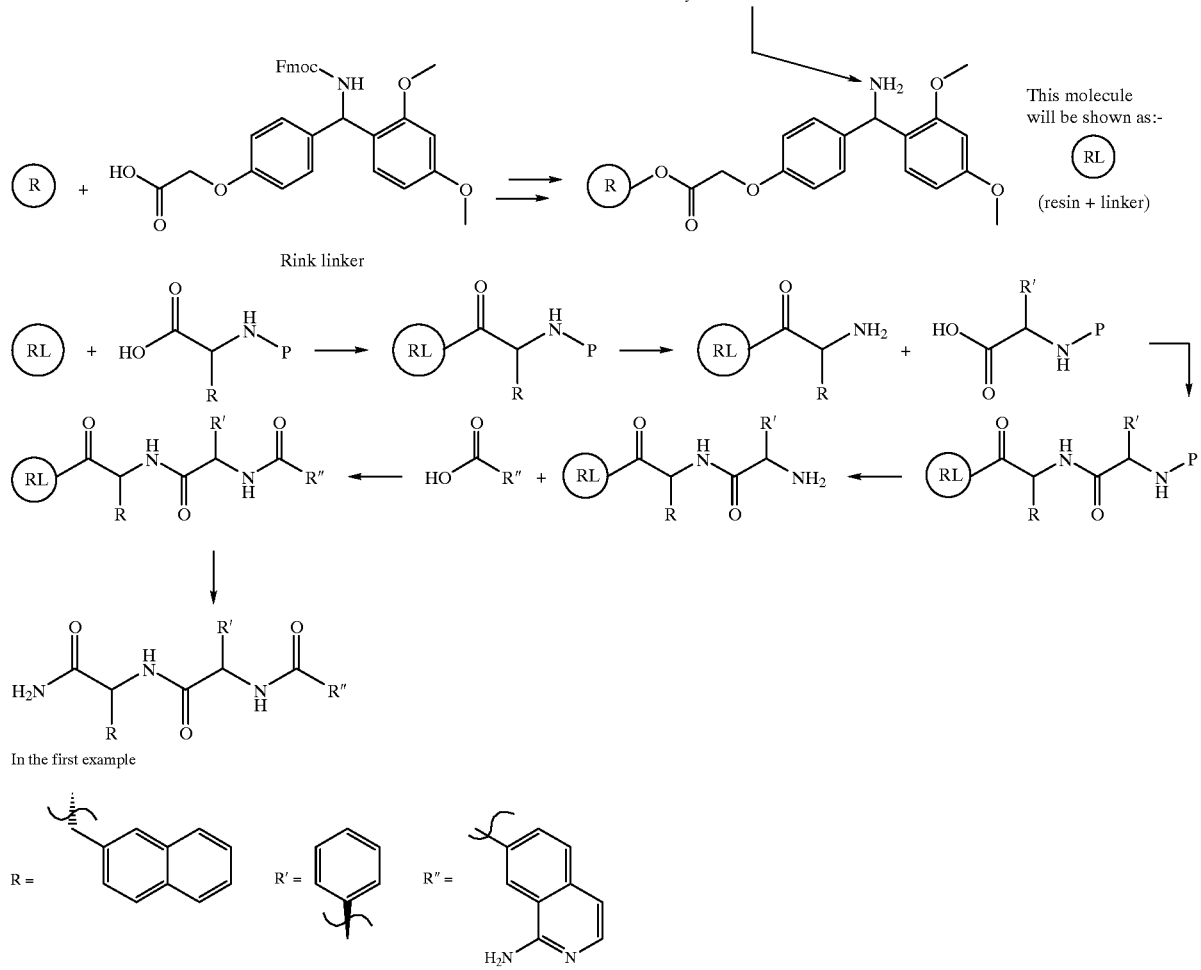
SCHEME 4
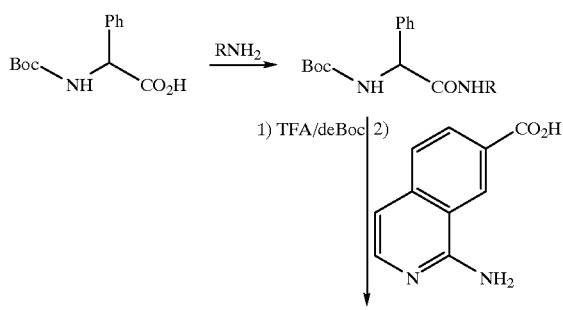
Scheme 5
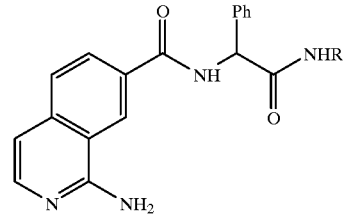
-continued
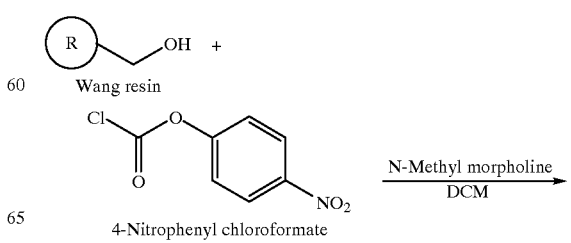

-continued

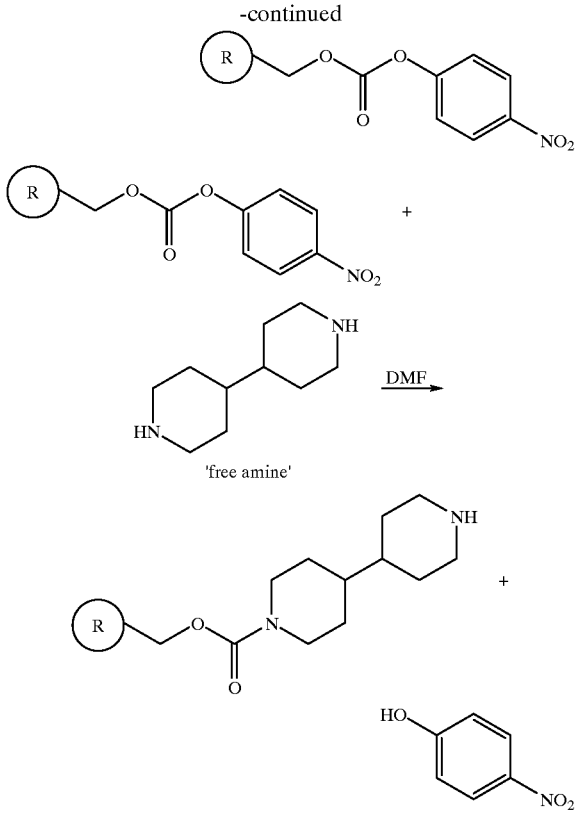

Carboxylic acids can then be attached to this resin.
On cleavage of the resin the product is of the form:-

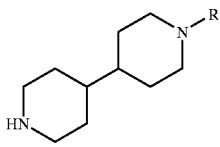

In all the syntheses illustrated in Schemes 1 to 5 the coupling reactions can of course be effected using an activated form of the carbonyl compound e.g. an acid chloride or active ester.

Where Y and L taken together form a cyclic amide group this can be conveniently introduced by reacting an Lp group carrying a secondary amine with an active side chain with a suitable amino acid. Cyclisation can be base induced via nucleophilic attack of the alpha atom on a leaving group on the active side chain.

If necessary the amide linkage from isoquinoline to alpha atom can be reduced using an appropriate reducing agent employing the necessary protection.

Alternatively, the compounds of the invention where X—X is C—N or C—O can be prepared from compounds of formula $H_2NCH(R_7)R''$ or $HOCH(R_7)R''$ respectively, by condensation with an appropriately substituted isoquinoline, e.g. 1-amino-7-bromomethyl-isoquinoline, in the presence of a base, where R'' is $L+Lp(D)_n$ or a functionality which can be converted to such by methods herein described.

Compounds of the invention where X—X is C—N can also be prepared from compounds of the formula $H_2NCH(R^7)R''$ by condensation with an appropriately substituted isoquinoline aldehyde or ketone, e.g. 1-amino-isoquinoline-7-carboxaldehyde, in the presence of a reducing agent such as sodium borohydride or sodium triacetoxyborohydride.

Alternatively, the compounds of the invention be prepared from compounds of formula $NH_2CH(R_7)COOH$ which can be conveniently reduced to an alcohol by reaction with isobutylchloroformate and reduction with sodium borohydride using suitable protection if necessary.

Such an alcohol can be reacted using suitable protection, to introduce the Lp group by reactions such as:
  alkylation with an alkyl halide in the presence of a base;
  reaction with diethyl azodicarboxylate/triphenylphosphine and a hydroxylated aryl compound;
  by reaction with an activated carboxylic acid (e.g. an acid chloride) or with a carboxylic acid and diethylazodicarboxylate/triphenylphosphine;
  by reaction with an isocyanate; and
  by treatment with methanesulphonyl chloride or trifluoromethanesulphonic anhydride and reaction with an amine, or with a thiol optionally followed by oxidation, e.g. with potassium metaperiodate or hydrogen peroxide.

In this way compounds with linkages of —$CH_2$—O—, —$CH_2$—C—CO—, —$CH_2$—O—CO—$NR_1$—, —$CH_2$—$NR_1$—, —$CH_2$—S—, —$CH_2$—SO— and —$CH_2$—$SO_2$— between the alpha carbon and the lipophilic group may be produced. These compounds can then be coupled with 1-amino-7-isoquinoline carboxylic acid TFA salt.

Alternatively the alcohol can be oxidized to form a corresponding aldehyde (e.g. by oxidation with manganese dioxide or DMSO/oxalyl chloride or DMSO/$SO_3$ or Dess-Martin reagent) which may be reacted to introduce the Lp group by reactions such as:
  reaction with Wittig reagents or Horner-Emmons reagents, optionally followed by reduction of the resulting carbon:carbon double bond using $H_2$/Pd-carbon;
  reaction with an organometallic, eg a Grignard reagent, optionally followed by reaction on the resulting hydroxyl group, such as oxidation (eg with $MnO_2$, DMSO/oxalyl chloride or Dess-Martin reagent), alkylation (eg with an alkyl halide in the presence of a base in a solvent such as DMF), arylation (eg with diethylazodicarboxylate/triphenyl phosphine and a hydroxyaryl compound), ester formation (eg with an acid chloride or with a carboxylic acid and diethylazido dicarboxylate/triphenyl phosphine), or carbamate formation (eg with an isocyanate);
  by reaction with an amine followed by reduction, e.g. with sodium cyanoborohydride;
  by reaction with a hydrazine; or by reaction with a carbazide.

In this way compounds with linkages of —CH═$CR_1$—, —$CH_2$—$CHR_1$—, —CHOH—, —$CHR_1$—O—, —$CHR_1$—O—CO—, —$CHR_1$—O—CO—$NR_1$—, —CO—, —$CH_2$—$NR_1$—, —CH═N—$NR_1$— and —CH═N—$NR_1$—CO—$NR_1$— between the alpha carbon and the lipophilic group may be produced. Again the resulting compounds could then be coupled to the isoquinoline derivative.

The transformation of alcohol to amine referred to above may be used to produce an amine reagent for lipophilic group introduction, e.g. a compound $NH_2$—$CH(R_7)$—$CH_2$—$NR_1H$.

Such an amine reagent may be reacted to introduce the lipophilic group, e.g. by acylation with an acid halide or activated ester, by reaction with isocyanate, by reaction with an isothiocyanate, or by reaction with a sulphonyl chloride. In this way compounds with linkages of —$CH_2NR_1$—CO—, —$CH_2$—$NR_1$—CO—$NR_1$—, —$CH_2NR_1$—CS—$NR_1$— and —$CH_2NR_1$—$SO_2$— between the alpha carbon and the lipophilic groups may be produced.

The transformation of acid to amide referred to above may be used to produce an amide reagent for introduction of the Lp group, e.g. a compound NH$_2$—CH(R$_1$)—CONH$_2$.

Such amides may be reacted to introduce lipophilic groups, e.g. by reaction with a haloketone (e.g. phenacyl bromide). This provides a linkage

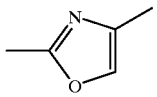

from alpha carbon to lipophilic group.

Analogously the amide may be transformed to a thioamide by reaction with Lawesson's reagent and then reacted with a haloketone to form a linkage

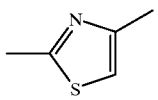

The amide reagent may likewise be transformed to a nitrile reagent by dehydration, e.g. with trifluoroacetic anhydride. The nitrile reagent may be reacted with hydrazine then with acyl halide and then cyclized, (e.g. with trifluoroacetic anhydride) to produce a linkage

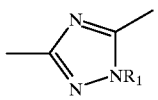

Alternatively it may be treated with hydroxylamine then reacted with acyl halide and cyclized (e.g. with trifluoroacetic anhydride) to produce a linkage

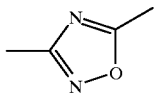

The hydrazide produced by reaction of a carboxylic acid reagent with hydrazine discussed above may likewise be used as a reagent for lipophilic group introduction, e.g. as a compound of formula NH$_2$—CH(R$_i$)—CO—NR$_1$—N(R$_1$)$_2$.

Thus the hydrazide reagent can be reacted with an acyl halide and cyclized, e.g. with trifluoroacetic anhydride to yield a linkage

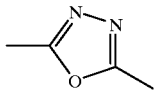

or reacted with an acyl halide or an isocyanate to yield linkages —CO—NR$_1$—NR$_1$—CO— and —CO—NR$_1$—NR$_1$—CO—NR$_1$— respectively.

Alternatively the hydrazide may be transformed by reaction with Lawesson's reagent and then reacted with an acyl halide and cyclized (e.g. with trifluoroacetic anhydride) to produce the linkage

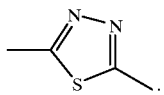

An alternative route to these compounds is to carry out any of the above chemical reactions to incorporate the lipophilic group (and optional H bond donor) into a protected intermediate such as a compound of formula (IV).

(IV)

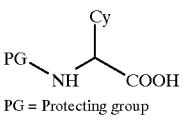

PG = Protecting group

The protecting group may then be removed before coupling of the 1-amino-7-carboxyisoquinoline (optionally protected).

A starting reagent for lipophilic group introduction where the alpha atom is nitrogen may be produced for example by reaction of a beta protected hydrazine (such protection to be chosen as to be compatible with the subsequent reagents to be employed) with phosgene, diphosgene, triphosgene or N,N' carbonyl diimidazole to give a reactive compound of the type:

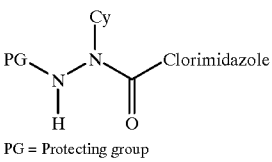

PG = Protecting group

This intermediate may be used as has been described above for the carboxylic starting reagents where the alpha atom is carbon.

Removal of the protecting group by standard methods and coupling with an activated 1-amino-7-carboxyisoquinoline will give compounds of the type

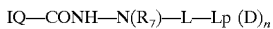

IQ—CONH—N(R$_7$)—L—Lp (D)$_n$ (where R$_7$, L, Lp and D are as defined above and IQ is a 1-aminoisoquinoline linked in the 7-position).

Thus viewed from a further aspect the invention provides a process for the preparation of a compound according to the invention which process comprises coupling a carbonyl attached group to 1-amino-7-carboxyisoquinoline.

The compounds of the invention may be administered by any convenient route, e.g. into the gastrointestinal tract (e.g. rectally or orally), the nose, lungs, musculature or vasculature or transdermally. The compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. Preferably the compositions will be sterile when in a solution or suspension form suitable for injection or infusion. Such compositions form a further aspect of the invention.

Viewed from this aspect the invention provides a pharmaceutical composition comprising a serine protease inhibitor according to the invention together with at least one pharmaceutically acceptable carrier or excipient.

Viewed from a further aspect the invention provides the use of a serine protease inhibitor according to the invention for the manufacture of a medicament for use in a method of treatment of the human or non-human animal body (e.g. a mammalian, avian or reptilian body) to combat a condition responsive to a serine protease inhibitor (e.g. a condition such as a thrombotic disorder responsive to a factor Xa inhibitor), said method comprising administering to said body an effective amount of a serine protease inhibitor according to the invention.

The dosage of the inhibitor compound of the invention will depend upon the nature and severity of the condition being treated, the administration route and the size and species of the patient. However in general, quantities of from 0.01 to 100 μmol/kg bodyweight will be administered.

All publications referred to herein are hereby incorporated by reference.

The invention will now be described further with reference to the following non-limiting Examples.

EXPERIMENTAL

Abbreviations used follow IUPAC-IUB nomenclature. Additional abbreviations are Hplc, high-performance liquid chromatography; DMF, dimethylformamide; DCM, dichloromethane; HAOt, 1-hydroxy-7-azabenzotriazole; HATU, [O—(7-azabenzotriazol-1-yl)-1,1,3,3-tetramethyluronium hexafluorophosphate]; Fmoc, 9-Fluorenylmethoxycarbonyl; HOBt, 1-hydroxybenzotriazole; TBTU, 2-(1H-(benzotriazol-1-yl)-1,1,3,3-tetramethyluroniumtetrafluoroborate; DIPEA, diisopropylethylamine; Boc, tertiary butyloxycarbonyl; DIPCI, diisopropylcarbodiimide; DBU, 1,8-diazabicyclo[5.4.0]undec-7-ene; TEA, triethylamine; EDC, 1-(3-dimethylaminopropyl)-3-ethylcarbodiimide hydrochloride; Rink linker, p-[(R,S)-α-[1-(9H-Fluoren-9-yl)methoxyformamido]-2,4-dimethoxybenzyl]phenyl acetic acid; TFA, trifluoroacetic acid; MALDI-TOF, Matrix assisted laser desorption ionisation—time of flight mass spectrometry; and RT, retention time. Unless otherwise indicated amino acid derivatives, resins and coupling reagents were obtained from Novabiochem (Nottingham, UK) and other solvents and reagents from Rathburn (Walkerburn, UK) or Aldrich (Gillingham, UK) and were used without further purification. All solution concentrations are expressed as % Vol./% Vol. unless otherwise stated.

Purification: Purification was by gradient reverse phase Hplc on a Waters Deltaprep 4000 at a flow rate of 50 ml/min. using a Deltapak C18 radial compression column (40 mm×210 mm, 10–15 mm particle size). Eluant A consisted of aqTFA (0.1%) and eluant B 90% MeCN in aqTFA (0.1%) with gradient elution (Gradient 1, 0 min. 20% B then 20% to 100% over 36 min., Gradient 2, 0 min. 5% B for 1 min. then 5% B to 20% B over 4 min., then 20% to 60% over 32 min. or Gradient 3, 0 min. 20% B then 20% to 100% over 15 min.). Fractions were analysed by analytical Hplc and MALDI-TOF or electrospray LCMS before pooling those with >95% purity for lyophilisation.

Analysis: Analytical Hplc was on a Shimadzu LC6 gradient system equipped with an autosampler, a variable wavelength detector at flow rates of 0.4 ml/min. Eluents A and B as for preparative Hplc. Columns used were Techogell5 C18 (2×150 mm)(Hplc Technology), Magellan C8 column (2.1× 150 mm, 5 mm particle size) (Phenomenex). Purified products were further analysed by MALDI-TOF and nmr.

Synthesis of Inhibitors

Method 1: Using a solid phase strategy on a Protein Technologies, Symphony Multiple Peptide Synthesiser by attachment of bis amino compounds to Peg-2-chlorotrityl chloride resin: 2-Chlorotrityl chloride resin was typically treated with greater than 2 fold excess of the di-amine in dry DCM. The resin was further modified by the attachment of acids. Activation of Fmoc protected amino acid (2-Seq) was by TBTU/DIPEA, all couplings (minimum 120 min.) were carried out in DMF. Deprotection of the Fmoc group was achieved with 20% piperidine in DMF. Other acid substituents were added as the HOBt or HOAt esters either by activation with HBTU/HATU or DIPCI with or without Boc protection of amino groups. Cleavage of the products from the resin was by treatment (30 min., ambient) with 10% triethylsilane in TFA, filtration, evaporation and trituration with diethylether.

Synthesis using the Symphony Multiple Peptide Synthesiser.

The Symphony Multiple Peptide Synthesiser is charged with DMF, DCM, TBTU in DMF(450 mM), DIPEA in DMF (900 mM), 20% piperidine in DMF. Resins are held in plastic reaction vessels that allow the introduction of reagents and solvents and nitrogen for agitation or air drying.

A typical synthesis cycle on the Symphony is as follows:

The reaction vessel containing the resin (0.1 mmol) is charged with the Fmoc protected amino acid (0.5 mmol) and then this is dissolved in DMF (2.5 ml), treated with TBTU (0.56 mmol, 1.25 ml) and DIPEA (1.1 mmol, 1.25 ml) and agitated with nitrogen for 2 hours (agitation times may vary). After coupling, the resin is washed with DMF (6×5 ml) then deprotected with 20% piperidine in DMF (2×5 ml for 1 min. each, then 1×5 ml for 8 min.). The resin is then washed with DMF (6×5 ml).

Example 1

1-Aminoisoquinolin-7-oyl-D-phenylglycine-4-aminomethylcyclohexyl methylamide

Bis-1,4-aminomethylcyclohexane(2 ml) was added to 2 chlorotrityl chloride resin (1.2 mmol/g, 0.73 g) pre swollen in dry DCM (4 ml). After 2 h the resin was washed with DCM (6×5 ml), DMF (6×5 ml) and DCM (6×5 ml). The resin was then air dried to allow aliquots to be taken.

The bis-1,4-aminomethylcyclohexane 2-chlorotrityl resin (0.1 mmol) was treated with Fmoc-D-Phenylglycine (0.5 mmol, 187 mg), DMF(2.5 ml), TBTU in DMF(1.25 ml of a 450 mM solution) and DIPEA in DMF (1.25 ml of a 900 mM solution). The mixture was agitated with nitrogen for 2 hours. Deprotection and washing as above.

A solution of 1-aminoisoquinoline-7-carboxylic acid trifluoroacetic acid salt (150 mg 0.5 mmole ) (Example 88) in dry dimethylformamide (DMF) was treated successively with HOAt (102 mg 0.75 mmole ) and EDC (115 mg 0.6 mmole ) and stirred at room temperature for 10 min. The mixture was transferred to the reaction vessel on the Symphony and agitated for 10 hours with nitrogen. The resin was washed with DMF (6×5 ml), DCM (6×5 ml) and air dried. The product was cleaved from the resin with 10% triethylsilane in TFA (10 ml) for 30 minutes, the resin filtered off and the TFA solution evaporated to dryness and triturated with diethyl ether to give the crude product. The crude product was dissolved in water (10 ml), filtered and purified by preparative reverse phase Hplc.

$^1$H nmr (CD$_3$CN) Mixture of cyclohexyl cis and trans isomers. 8.65 (1H,s); 8.10 (1H,d); 7.75 (1H,d); 7.35 (1H,d); 7.30 (2H,m); 7.15 (3H, m); 7.00 (1H,d); 5.40 (1H, s); 3.25–2.55 (4H, m); 1.7–0.9 (7H, m); 0.7–0.5

(3H, m) MS TOF 446 (M+1$^{30}$). Hplc (Magellan C8, Gradient 3, water/acetonitrile/TFA) rt 8.23 min.

Method 2: By solid phase strategy on a Protein Technologies, Symphony Multiple Peptide Synthesiser using Fmoc amino acids attached to Peg-2-chlorotrityl chloride resin: Typically the 2-chlorotrityl chloride resin was treated with a 2 fold excess of the Fmoc amino acid in a 1:1 mixture of DMF and dry DCM and DIPEA (2 eq.). The resin was washed with DMF/DCM and deprotected with 20% piperidine in DMF before further modification. The resin was further modified by the attachment of acids. Activation of Fmoc protected amino acids (2–5 eq) was by activation with TBTU/DIPEA, all couplings (minimum 120 min.) were carried out in DMF. Deprotection of the Fmoc group was achieved with 20% piperidine in DMF. Other acid substituents were added as the HOBt or HOAt esters either by activation with HBTU/HATU or DIPCI with or without Boc protection of amino groups. Cleavage of the products from the resin was by treatment (30 min., ambient) with 10% triethylsilane in TFA, filtration, evaporation and trituration with ether.

Example 2

1-Aminoisoquinolin-7-oyl-D-phenylglycinyl-D-2-naphthylalaninylglycine

Fmoc Glycine (0.2 mmol, 59 mg.) in DMF (2 ml) was added to 2 chlorotrityl chloride resin (1.0 mmol/g, 0.1 g) pre swollen in dry DCM (2 ml), then DIPEA (0.2 mmol,). After 2 h the resin was washed with DCM (6×5 ml), DMF (6×5 ml) and DCM (6×5 ml). The resin was then air dried to allow aliquots to be taken for further modification.

On the Symphony Fmoc-Glycyl-2-chlorotrityl resin (0.1 mmol) was deprotected with 20% piperidine in DMF and washed with DMF(6×5 ml) then treated with Fmoc-D-2-naphthylalanine (0.5 mmol 220 mg), DMF(2.5 ml), TBTU in DMF(1.25 ml of a 450 mM solution) and DIPEA in DMF (1.25 ml of a 900 mM solution). The mixture was agitated with nitrogen for 2 hours. Deprotection and washing as above. The resin was then treated Fmoc-D-Phenylglycine (0.5 mmol 187 mg), DMF(2.5 ml), TBTU in DMF(1.25 ml of a 450 mM solution) and DIPEA in DMF (1.25 ml of a 900 mM solution). The mixture was agitated with nitrogen for 2 hours. Deprotection and washing as above.

A solution of 1-aminoisoquinoline-7-carboxylic acid trifluoroacetic acid salt (150 mg 0.5 mmole) (Example 88) in dry dimethylformamide (DMF) was treated successively with HOAt (102 mg 0.75 mmole) and EDC (115 mg 0.6 mmole) and stirred at room temperature for 10 min. The mixture was transferred to the reaction vessel on the Symphony and agitated for 10 hours with nitrogen. The resin was then washed with DMF(6×5 ml), DCM (6×5 ml) and air dried. The product was cleaved from the resin with 10% triethylsilane in TFA (10 ml) for 30 minutes, the resin filtered off, the TFA solution evaporated to dryness and triturated with diethyl ether to give the crude product. The crude product was then dissolved in water (10 ml), filtered and purified by preparative reverse phase Hplc.

1H nmr (DMSO) 8.80 (1H,s); 8.20 (1H,d); 7.85 (1H,d); 7.55 (6H,m); 7.35 (1H, d); 7.20 (7H, m); 5.80 (1H, s); 4.70 (1H,m); 3.85 (2H,m, obscured by solvent); 3.15 (2H,m). MS TOF 576 (M+1+). Hplc (Magellan C8, Gradient 3, water/acetonitrile/TFA) rt 10.98 min.

Other compounds made by the above method:

Example 3

1-Aminoisoquinolin-7-oyl-D-phenylglycinyl-D-2-naphthylalaninyl-D-proline 1H nmr (DMSO) 8.35 (1H,s); 7.90 (1H,d); 7.65 (1H,d); 7.45 (5H,m); 7.35 (1H, d); 7.20 (1H,d); 7.05 (7H, m); 5.45 (1H, s); 4.75 (1H,m); 4.10 (1H,m); 3.45 (2H,m, obscured by solvent); 3.00 (2H,m) 2.00 (1H,m); 1.70 (2H,m); 1.45 (1H, m). MS TOF 576 (M+1+). Hplc (Magellan C8, Gradient 3, water/acetonitrile/TFA) rt 11.19 min.

Method 3: By solid phase strategy on a Protein Technologies, Symphony Multiple Peptide Synthesiser using Fmoc amino acids attached to TentaGel S-resin (Rapp Polymere) via the Rink amide linker: Typically the TentaGel resin was treated with a 5 fold excess of the Rink linker, TBTU (1 eq.), DIPEA (2 eq.) in DMF for a minimum of 120 mins. The resin was washed with DMF and deprotected with 20% piperidine in DMF before further modification. The resin was further modified by the attachment of acids. Activation of Fmoc protected amino acid (2–5 eq) was by TBTU/DIPEA, all couplings (minimum 120 min.) were carried out in DMF. Deprotection of the Fmoc group was achieved with 20% piperidine in DMF. Other acid substituents were added as the HOBt or HOAt esters either by activation with HBTU/HATU or DIPCI with or without Boc protection of amino groups. Cleavage of the products from the resin was by treatment (30 min., ambient) with 10% triethylsilane in TFA, filtration, evaporation and trituration with ether.

Example 4

1-Aminoisoquinolin-7-oyl-D-phenylglycinyl-D-2-naphthylalanine amide

On the Symphony TentaGel S -NH2 resin (0.1 mmol, 400 mg, 0.24 mmol./g) was treated with Rink linker (0.5 mmol, 270 mg), DMF(2.5 ml), TBTU in DMF(1.25 ml of a 450 mM solution) and DIPEA in DMF (1.25 ml of a 900 mM solution). The mixture was agitated with nitrogen for 2 hours. Deprotection and washing as above.

On the Symphony Rink-TentaGel resin (0.1 mmol) was then treated with Fmoc-D-naphthylalanine (0.5 mmol, 194 mg), DMF(2.5 ml), TBTU in DMF(1.25 ml of a 450 mM solution) and DIPEA in DMF (1.25 ml of a 900 mM solution). The mixture was agitated with nitrogen for 2 hours. Deprotection and washing as above.

The resin (0.1 mmol) was then treated with Fmoc-D-Phenylglycine (0.5 mmol, 187 mg), DMF(2.5 ml), TBTU in DMF(1.25 ml of a 450 mM solution) and DIPEA in DMF (1.25 ml of a 900 mM solution). The mixture was agitated with nitrogen for 2 hours. Deprotection and washing as above.

A sample of 1-aminoisoquinoline-7-carboxylic acid trifluoroacetic acid salt (150 mg 0.5 mmole) (Example 88) in dry dimethylformamide (DMF) was treated successively with HOAt (102 mg 0.75 mmole) and EDC (115 mg 0.6 mmole) and stirred at room temperature for 10 min. The mixture was then transferred to the reaction vessel on the Symphony and agitated for 10 hours with nitrogen. The resin was then washed with DMF (6×5 ml), DCM (6×5 ml) and air dried. The product was cleaved from the resin with 10% triethylsilane in TFA (10 ml) for 30 minutes, the resin filtered off, the TFA solution evaporated to dryness and triturated with diethyl ether to give the crude product. The crude product was then dissolved in water (10 ml), filtered and purified by preparative reverse phase Hplc.

1H nmr (CD$_3$CN) 8.45 (1H,s); 8.05 (1H,d); 7.85 (1H,d); 7.55 (5H,m); 7.45 (1H, d); 7.25 (1H,d); 7.10 (7H, broad m); 5.45 (1H, s); 4.65 (1H,m); 3.15 (2H,m). MS TOF 518 (M+1+). Hplc (Magellan C8, Gradient 3, water/acetonitrile/TFA) rt 10.67 min.

Method 4: By solution phase strategy: Typically an activated Boc-amino acid was treated with an amine (primary or secondary) or alcohol (1 eq.). Activation of Boc protected amino acid was by HATU or TBTU/DIPEA (1:2), all couplings (minimum 120 min.) were carried out in DMF. After an aqueous work up the deprotection of the Boc group was achieved with TFA. Other acid substituents were added as the HOBt or HOAt esters either by activation with HBTU/HATU, EDC or DIPCI with or without Boc protection of amino groups. The final products were purified by preparative reverse phase Hplc.

Example 5

1-Aminoisoquinolin-7-oyl-D-phenylglycine-4-methylbenzylamide

Boc D-phenylglycine (251 mg, 1 mmol.) was dissolved in DMF(3 ml) with HATU (380 mg., 1 mmol.) and DIPEA(350 µl., 2 mmol.). To this mixture was added 4-methylbenzyl-amine(121 mg., 1 mmol.) and DIPEA (1701 µl., 1 mmol.). The mixture was stirred overnight. The mixture was then taken up into ethylacetate and washed with water, sodium carbonate solution, water, 10% hydrochloric acid solution and water. The ethylacetate was evaporated without drying and treated immediately with TFA for 30 min. The TFA was then evaporated to dryness and the product triturated with diethylether. TEA(1 ml) was added and evaporated to dryness. A solution of 1-aminoisoquinoline-7-carboxylic acid trifluoroacetic acid salt (300 mg 1mmole) (Example 88) in dry dimethylformamide (DMF) was treated successively with HOAt (204 mg 1.5 mmole ) and EDC (230 mg 1.2 mmole ) and stirred at room temperature for 10 min. The mixture was then added to the D-phenylglycine-4-methylbenzylamide and stirred overnight. The crude product was dissolved in water/acetonitrile (20 ml), filtered and purified by preparative Hplc to yield pure product.

1H nmr (CD$_3$CN) 8.86 (1H, s); 8.32 (1H, d); 7.96 (1H, d); 7.60 (1H, d); 7.46 (5H, m); 7.24 (1H,d); 7.06 (4H, m); 5.64 (1H, s); 4.31 (2H, m); 2.29 (3H, m). MS TOF 426 (M+1$^+$). Hplc (Magellan C8, Gradient 3, water/acetonitrile/TFA) rt 11.00 min.

Other compounds made by the above method:

Example 6

1-Aminoisoquinolin-7-oyl-D-phenylalanine-4-methylbenzylamide 1H nmr (CD$_3$CN) 8.65 (1H, s); 8.05 (1H, d); 7.80 (1H, d); 7.45 (1H, d); 7.10 (6H, m); 6.95 (4H, m); 4.70 (1H, m); 4.15 (2H, m); 2.95 (2H,m); 2.20 (3H, m). MS TOF 440 (M+1$^+$). Hplc (Magellan C8, Gradient 3, water/acetonitrile/TFA) rt 11.40 min.

Example 7

1-Aminoisoquinoline-7-oyl-D-phenylglycine-4-benzoyl piperidinamide 1H nmr (CD$_3$CN) mixture of rotomers 8.85 (1H,d); 8.25 (1H,m); 8.00 (1H, s); 7.85 (2H, m); 7.58 (2H, m); 7.40(7H, m); 7.20 (1H, d); 6.03 (1H, s); 4.50 (1H, m); 3.15 (1H,m); 2.80 (3H,m); 1.60 (2H,m); 1.42 (1H,m); 0.45 (1H,m). MS TOF 493 (M+1$^+$). Hplc (Magellan C8, Gradient 3, water/acetonitrile/TFA) rt 11.48 min.

Example 8

1-Aminoisoquinolin-7-oyl-D-phenylglycine-4-(4'-pyridyl) piperazinamide 1H nmr (CD$_3$CN) 8.70 (1H,s); 8.15 (1H,d); 7.90 (2H, d); 7.85 (1H, d); 7.45 (1H, d); 7.35 (5H, m); 7.10 (1H,d); 6.80 (2H,d); 6.00 (1H, s); 3.70–3.10 (broad 8H,m). MS TOF 467 (M+1$^+$). Hplc (Magellan C8, Gradient 1, water/acetonitrile/TFA) rt 9.00 min.

Example 9

1-Aminoisoquinolin-7-oyl-D-phenylglycine-4-(4'-aminophenyl) piperazinamide 1H nmr (CD$_3$CN) 8.80 (1H,s); 8.25 (1H,d); 7.95 (1H, d) 7.55 (1H, d); 7.35 (5H, m); 7.20 (3H, d); 7.00 (2H,d); 6.10 (1H, s); 3.70–2.60 (several broad 8H,m). MS TOF 481 (M+1$^+$). Hplc (Magellan C8, Gradient 3, water/acetonitrile/TFA) rt 9.91 min.

Example 10

1-Aminoisoquinolin-7-oyl-D-phenylglycine-4-phenyl piperazinamide 1H nmr (CD$_3$CN) 8.70 (1H,d); 8.25 (1H,d); 7.90 (1H, d); 7.60 (3H, d); 7.40 (3H, m); 7. 25 (2H, m); 7.15(1H, d); 6.90 (3H,m); 6.15 (1H, s); 3.85 (1H, m); 3.70 (2H,m); 3.55 (1H,m); 3.15 (3H,m); 2.65 (1H,m). MS TOF 466 (M+1$^+$). Hplc (Magellan C8, Gradient 3, water/acetonitrile/TFA) rt 10.65 min.

Example 11

1-Aminoisoquinolin-7-oyl-D-phenylglycine-4-(3-pyridyl) piperazinamide 1H nmr (CD$_3$CN) 8.75 (1H,s); 8.15 (2H, m); 7.90 (1H, d); 7.80 (2H, m); 7.65 (1H, m); 7.40 (3H, m); 7.25 (3H, m); 7.10 (1H,d); 6.05 (1H, S); 3.70 (3H, m); 3.30 (4H,m); 2.80 (1H,m). MS TOF 467 (M+1$^+$). Hplc (Magellan C8, Gradient 3, water/acetonitrile/TFA) rt 8.30 min.

Example 12

1-Aminoisoquinolin-7-oyl-D-phenylglycine-4-(2-pyridyl) piperazinamide 1H nmr (CD$_3$CN) 8.75 (1H,s); 8.30 (1H,d); 8.20 (1H, d); 8.10 (1H, d); 7.90 (2H m); 7.60 (3H, m); 7.45 (3H, m); 7.20 (1H,d); 7.10 (1H,d); 6.90 (1H,m); 6.20 (1H, s); 3.80 (3H, m); 3.55 (4H,m); 3.25 (1H,m). MS TOF 467 (M+1$^+$). Hplc (Magellan C8, Gradient 3, water/acetonitrile/TFA) rt 8.68 min.

Example 13

1-Aminoisoquinolin-7-oyl-D-phenylglycine-4-(3-trifluorophenyl) piperazinamide 1H nmr (CD$_3$OD) 8.85 (1H,s); 8.25 (1H,d); 7.90 (1H, d); 7.45 (3H, m); 7.30 (4H, m); 7.15 (1H, d); 7.00 (3H, m); 6.15 (1H, s); 3.80 (1H, m); 3.65 (2H,m); 3.50 (1H,m); 3.15 (2H,m); 3.05 (1H,m); 2.65 (1H,m). MS TOF 534 (M+1$^+$). Hplc (Magellan C8, Gradient 3, water/acetonitrile/TFA) rt 12.72 min.

Example 14

1-Aminoisoquinolin-7-oyl-D-phenylglycine-4-(2-methoxyphenyl) piperazinamide 1H nmr (CD$_3$CN) 8.85 (1H,s); 8.25 (1H,d); 7.85 (1H, d); 7.50 (1H, d); 7.45 (2H, m); 7.30 (3H, m); 7.15 (1H,d); 6.95 (1H,m); 6.85 (1H,d); 6.80 (2H,m); 6.10 (1H, s); 3.70 (3H, m); 3.50 (1H,m); 3.00 (3H,m); 2.45 (1H,m). MS TOF 496

Example 15

1-Aminoisoquinolin-7-oyl-D-phenylglycine-4-(2-methylphenyl) piperazinamide 1H nmr (CD$_3$CN) 8.85 (1H,s); 8.25 (1H,d); 7.85 (1H, d); 7.55 (1H, d); 7.45 (2H, m); 7.35 (3H, m); 7.15 (1H,d); 6.95 (2H,m); 6.80 (2H,m); 6.10 (1H, s); 3.80 (1H, m); 3.60 (2H,m); 3.45 (1H,m); 2.75 (3H,m); 2.30 (1H,m). MS TOF 480 (M+1$^+$). Hplc (Magellan C8, Gradient 3, water/acetonitrile/TFA) rt 9.75 min.

Example 16

1-Aminoisoquinolin-7-oyl-D-phenylglycine-4-(-3,4 methylenedioxybenzyl) piperazinamide 1H nmr (CD$_3$CN) 8.55 (1H,s); 8.15 (1H,d); 7.70 (1H, d); 7.40 (1H, d); 7.30 (5H, m); 7.00 (1H,d); 6.75 (1H,s); 6.70 (2H,s); 5.85 (1H, s); 3.90 (2H, s); 3.60 (2H,m); 3.00–2.00 (broad signal 8H). MS TOF 524 (M+1$^+$). Hplc (Magellan C8, Gradient 3, water/acetonitrile/TFA) rt 9.25 min.

Example 17

1-Aminoisoquinolin-7-oyl-D-phenylglycine-4-(4'-fluorophenyl) piperazinamide 1H nmr (CD$_3$CN) 8.75 (1H,s); 8.20 (1H,d); 7.85 (1H, d); 7.55 (1H, d); 7.40 (5H, m); 7.15 (1H,d); 7.05 (4H,m); 6.05 (1H, s); 3.80 (3H, m, obscured by solvent); 3.55 (1H,m); 3.25 (2H,m); 3.10 (1H,m); 2.60 (1H,m). MS TOF 484 (M+1$^+$). Hplc (Magellan C8, Gradient 3, water/acetonitrile/TFA) rt 11.31 min.

Example 18

1-Aminoisoquinolin-7-oyl-D-phenylglycine-4-(2-chlorophenyl) piperazinamide 1H nmr (CD$_3$CN) 8.85 (1H,s); 8.45 (1H,d); 8.10 (1H, d); 7.75 (1H, d); 7.50 (6H, m);7.40 (2H,m); 7.20 (2H,m); 6.30 (1H, s); 4.00 (1H,m); 3.85 (2H,m); 3.70 (1H,m); 3.25 (1H,m); 3.10 (2H,m); 2.60 (1H,m). MS TOF 501 (M+1$^+$). Hplc (Magellan C8, Gradient 3, water/acetonitrile/TFA) rt 12.66 min.

Example 19

1-Aminoisoquinolin-7-oyl-D-phenylglycine-4-(2-pyrimidyl) piperazinamide 1H nmr (CD$_3$CN) 8.85 (1Hgs); 8.35 (2H,d); 8.25 (1H,d); 7.90 (1H, d); 7.60 (1H, d); 7.45 (5H, m); 7.20 (1H,d); 6.65 (1H,t); 6.10 (1H, s); 3.90–3.50 (broad signal 6H); 3.50 (1H,m); 3.20 (1H,m). MS TOF 468 (M+1$^+$). Hplc (Magellan C8, Gradient 3, water/acetonitrile/TFA) rt 9.22 min.

Example 20

1-Aminoisoquinolin-7-oyl-D-phenylglycine piperidinamide 1H nmr (CD$_3$CN) 9.10 (1H,s); 8.80 (1H,d); 8.35 (1H,d); 8.00 (1H,d); 7.70 (1H, d); 7.50 (2H, d); 7.40 (5H, m); 7.25 (1H,d); 6.15 (1H, s); 3.70–3.30 (broad 4H,m); 1.60–100 (broad 6H, m). MS TOF 389 (M+1$^+$). Hplc (Magellan C8, Gradient 3, water/acetonitrile/TFA) rt 10.47 min.

Example 21

1-Aminoisoquinolin-7-oyl-D-phenylglycine-4-l4'-pyridyl) piperidinamide 1H nmr (CDCl$_3$) 9.05 (1H,s); 8.80 (1H,d); 8.60 (2H,m); 8.35 (1H,d); 8.00 (1H,d); 7.70 (1H, d); 7.55 (3H, m); 7.40 (5H, m); 7.25 (1H,d); 6.20 (1H, s); 4.70 (1H,m); 4.30–1.50 (broad 9H,m). MS TOF 466 (M+1$^+$). Hplc (Magellan C8, Gradient 3, water/acetonitrile/TFA) rt 9.58 min.

Example 22

1-Aminoisoquinolin-7-oyl-D-phenylglycine-4-phenoxypiperidinamide 1H nmr (DMSO) 9.05 (1H,s); 8.40 (1H,d); 8.05 (2H,m); 7.65 (1H,d); 7.55 (2H,m); 7.40 (3H, m); 7.25 (3H, m); 6.90 (3H, m); 6.10 (1H, s); 4.55 (1H,m); 3.85 (2H,m); 3.35 (2H,m); 1.90 (1H,m); 1.60 (1H,m); 1.30 (1H,m); 0.90 (1H, m). MS TOF 481 (M+130 ). Hplc (Magellan C8, Gradient 3, water/acetonitrile/TFA) rt 11.95 min.

Example 23

1-Aminoisoquinolin-7-oyl-D-phenylglycine-2(RS)-methylcyclohexamide 1H nmr (DMSO) Mixture of diastereomers (major reported) 9.00 (1H,s); 8.25 (1H,d); 7.95 (1H,d); 7.60 (1H,d); 7.45 (2H, m); 7.25 (4H, m); 5.60 (1H, s); 3.10 (1H,m); 1.80–0.8 (broad m, 9H) 0.40 (3H,m). MS TOF 417 (M+1+). Hplc (Magellan C8, Gradient 3, water/acetonitrile/TFA) rt 11.23 min.

Example 24

1-Aminoisoquinolin-7-oyl-D-phenylglycine-1-S-cyclohexylethylamnide 1H nmr (CD$_3$CN) 8.80 (1H,s); 8.25 (1H,d); 7.90 (1H,d); 7.50 (1H,d); 7.45 (2H, m); 7.30 (4H, m); 7.15 (1H,d); 5.35 (1H, s); 3.60 (1H,m); 1.70–0.50 (broad m, 11H) 1.00 (3H,d). MS TOF 431 (M+1$^+$). Hplc (Magellan C8, Gradient 3, water/acetonitrile/TFA) rt 11.09 min.

Example 25

1-Aminoisoquinolin-7-oyl-D-phenylglycine-4-methoxybenzylamide 1H nmr (CD$_3$CN) 8.60 (1H,s); 8.05 (1H,d); 7.70 (1H,d); 7.35 (1H,d); 7.30 (2H, m); 7.15 (3H, m); 7.00 (1H,d); 6.85 (2H,d); 6.60 (2H,d); 5.45 (1H, s); 4.10 (2H,m). MS TOF 441 (M+1$^+$). Hplc (Magellan C8, Gradient 3, water/acetonitrile/TFA) rt 10.91 min.

Example 26

1-Aminoisoquinolin-7-oyl-D-phenylglycine-3,4-methylenedioxybenzylamide 1H nmr (CD$_3$CN) 8.65 (1H,s); 8.25 (1H,d); 7.85 (1H,d); 7.45 (3H,m); 7.30 (3H, m); 7.15 (1H,d); 6.65 (3H,m); 5.55 (1H, s); 4.20 (2H,m). MS TOF 455 (M+1$^+$). Hplc (Magellan C8, Gradient 3, water/acetonitrile/TFA) rt 11.02 min.

Example 27

1-Aminoisoquinolin-7-oyl-D-phenylglycine-1-naphthylamide 1H nmr (CD$_3$CN) 8.45 (1H,s); 8.20 (1H,d); 7.80 (1H,d); 7.65 (1H,d); 7.60 (2H,m); 7.50 (1H,m); 7.4–7.0 (9H,m);

6.80 (1H,d); 5.80 (1H, s); 4.60 (2H,m). MS TOF 461 (M+1⁺). Hplc (Magellan C8, Gradient 3, water/acetonitrile/TFA) rt 11.61 min.

Example 28

1-Aminoisoquinolin-7-oyl-D-phenylglycine-1,2,3,4-tetrahydro-1-naphthylamide 1H nmr (CD$_3$CN) 8.75 (1H,s); 8.30 (1H,d); 7.95 (1H,d); 7.65 (2H,d); 7.40 (3H,m); 7.30 (1H,d); 7.10 (5H,m); 5.65 (1H, s); 5.10 (1H,m); 2.75 (2H,m) 2.4–1.5 (4H, broad m). MS TOF 451 (M+1⁺). Hplc (Magellan C8, Gradient 3, water/acetonitrile/TFA) rt 11.60 min.

Example 29

1-Aminoisoquinolin-7-oyl-D-phenylglycine-1-indanamide 1H nmr (CD$_3$CN) 8.75 (1H,s); 8.30 (1H,d); 7.95 (1H,d); 7.55 (3H,m); 7.40 (3H,m); 7.30 (1H,d); 7.20 (4H,m); 5.65 (1H, s); 5.40 (1H,m); 2.90 (2H,m) 2.50 (1H,m); 1.80 (1H, m). MS TOF 437 (M+1⁺). Hplc (Magellan C8, Gradient 3, water/acetonitrile/TFA) rt 11.26 min.

Example 30

1-Aminoisoquinolin-7-oyl-D-phenylglycine-1,2,3,4-tetrahydroisoquinolinamide 1H nmr (DMSO) 9.20 (1H,s); 8.55 (1H,d); 8.20 (1H,d); 7.95 (1H,d); 7.70 (2H,m); 7.55 (3H,m); 7.40 (1H,d); 7.25 (4H,m); 6.40 (1H, s); 4.80 (2H,m); 3.90 (2H,m) 3.90 (2H, m). MS TOF 437 (M+1+). Hplc (Magellan C8, Gradient 3, water/acetonitrile/TFA) rt 11.34 min.

Example 31

1-Aminoisoquinolin-7-oyl-D-phenylglycine-{3-(3-aminophenyl)methyl}anilide 1H nmr (DMSO) 9.00 (1H,s); 8.30 (1H,d); 7.95 (1H,d); 7.65 (1H,d); 7.50 (2H,m); 7.30 (4H,m); 7.15 (4H,m); 6.75 (4H,m); 5.75 (1H, s); 3.80 (2H,s). MS TOF 502 (M+1+). Hplc (Magellan C8, Gradient 3, water/acetonitrile/TFA) rt 9.48 min.

Example 32

1-Aminoisoquinolin-7-oyl-D-phenylglycine-3-acetylphenylanilide 1H nmr (DMSO) 8.85 (1H,s); 8.25 (1H,s); 8.10 (1H,d); 7.85 (2H,m); 7.75 (1H,d); 7.65 (3H,m); 7.40 (3H,m) 6.95 (2H,m); 5.95 (1H, s3; 2.50 (3H,s). MS TOF 439 (M+1+). Hplc (Magellan C8, Gradient 3, water/acetonitrile/TFA) rt 10.55 min.

Example 33

1-Aminoisoquinolin-7-oyl-D-phenylglycine-3(-1-hydroxyethyl)phenylanilide 1H nmr (DMSO) 8.95 (1H,s); 8.15 (1H,s); 7.95 (1H,d); 7.80 (1H,d); 7.65 (2H,d); 7.55 (1H,d); 7.45 (3H,m); 7.30 (1H,d); 7.05 (3H,m); 5.95 (1H, s); 4.75 (1H,m); 1.40 (3H,d). MS TOF 441 (M+1+). Hplc (Magellan C8, Gradient 3, water/acetonitrile/TFA) rt 10.03 min.

Example 34

1-Aminoisoquinolin-7-oyl-D-phenylglycine-4-(4'-chlorophenyl) piperazinamide 1H nmr (CD$_3$CN) 8.85 (1H,s); 8.30 (1H,d); 7.95 (1H, d); 7.65 (1H, d); 7.65 (2H,d); 7.50 (3H, m); 7.30 (3H,m); 7.00 (2H,d); 6.15 (1H, s); 3.95 (1H,m); 3.70 (3H, m); 3.25 (2H,m); 3.05 (1H,m); 2.55 (1H,m). MS TOF 501 (M+1⁺). Hplc (Magellan C8, Gradient 3, water/acetonitrile/TFA) rt 11.95 min.

Example 35

1-Aminoisoquinolin-7-oyl-D-phenylglycine-4-(4'-hydroxyphenyl) piperazinamide 1H nmr (CD$_3$CN) 8.85 (1H,s); 8.25 (1H,d); 7.95 (1H, d); 7.55 (3H, m); 7.45 (3H, m); 7.25 (3H,m); 6.90 (2H,d); 6.15 (1H, s); 3.95 (3H, m); 3.65 (1H,m, obscured by solvent); 3.40 (3H,m); 2.90 (1H,m). MS TOF 481 (M+1⁺). Hplc (Magellan C8, Gradient 3, water/acetonitrile/TFA) rt 7.84 min.

Example 36

1-Aminoisoquinolin-7-oyl-D-phenylglycine-4-(4'-nitrophenyl) piperazinamide 1H nmr (CD$_3$CN) 8.70 (1H,s); 8.15 (1H,d); 7.95 (2H,d); 8.80 (1H, d); 7.50 (3H, m); 7.30 (3H, m); 7.05 (1H,d); 6.70 (2H,d); 6.00 (1H, s); 3.60 (3H, m); 3.30 (4H,m); 2.80 (1H,m). MS TOF 511 (M+1⁺). Hplc (Magellan C8, Gradient 3, water/acetonitrile/TFA) rt 10.81 min.

Example 37

1-Aminoisoquinolin-7-oyl-D-phenylglycine-4-(4'-methylphenyl) piperazinamide 1H nmr (CD$_3$CN) 8.85 (1H,s); 8.45 (1H,d); 8.05 (1H, d); 7.70 (3H, m); 7.55 (3H, m); 7.35 (1H,d); 7.25 (2H,d); 7.00 (2H,d); 6.30 (1H, s); 3.95 (3H, m); 3.70 (1H,m); 3.25 (3H,m); 2.60 (1H,m); 2.40 (3H,s). MS TOF 480 (M+1⁺). Hplc (Magellan C8, Gradient 3, water/acetonitrile/TFA) rt 10.27 min.

Example 38

1-Aminoisoquinolin-7-oyl-D-phenylglycine-4-(4'-methoxyphenyl) piperazinamide 1H nmr (CD$_3$CN) 8.85 (1H,s); 8.25 (1H,d); 7.95 (1H, d); 7.55 (3H, m); 7.40 (3H, m); 7.20 (1H,d); 7.15 (2H,d); 6.95 (2H,d); 6.20 (1H, s); 3.85(3H,m); 3.75 (3H,s); 3.60 (1H,m); 3.30 (2H,m); 3.15 (1H,m); 2.75 (1H,m). MS TOF 496 (M+1⁺). Hplc (Magellan C8, Gradient 3, water/acetonitrile/TFA) rt 8.86 min.

Example 39

1-Aminoisoquinolin-7-oyl-D,L-4-fluorophenylglycine-4-(4'-fluorophenyl) piperazinamide 1H nmr (DMSO) 9.05 (1H,s); 8.35 (1H,d); 8.05 (1H, d); 7.70 (1H, d); 7.55 (2H, m); 7.25 (3H,m); 7.05 (2H,m); 6.90 (2H,m); 6.15 (1H, s); 3.60 (3H, m); 3.05 (3H,m); 2.90 (1H,m); 2.60 (1H,m). MS TOF 502 (M+1+). Hplc (Magellan C8, Gradient 3, water/acetonitrile/TFA) rt 11.13 min.

Example 40

1-Aminoisoquinolin-7-oyl-D-cyclohexylglycine-4-(4'-fluorophenyl) piperazinamide 1H nmr (DMSO) 9.05 (1H,d); 8.70 (1H,d); 8.05 (1H, d); 7.70 (1H, d); 7.30 (1H,d); 7.00 (4H, m); 4.90 (1H, m); 3.85

(2H,m); 3.70 (2H,m); 3.05 (4H, m); 1.90 (1H,m); 1.70 (4H,m); 1.15 (6H,m). MS TOF 490 (M+1+). Hplc (Magellan C8, Gradient 3, water/acetonitrile/TFA) rt 11.19 min.

Example 41

1-Aminoisoquinolin-7-oyl-D-phenylglycine-4-(3-chlorophenyl) piperazinamide 1H nmr (CD$_3$CN) 8.80 (1H,s); 8.25 (1H,d); 7.90 (1H, d); 7.50 (3H, m); 7.40 (3H, m); 7.20 (2H, m); 6.85 (3H, m); 6.15 (1H, s); 3.80 (1H, m); 3.65 (2H,m); 3.55 (1H,m) 3.20 (2H,m); 3.05 (1H,m); 2.55 (1H,m). MS TOF 501 (M+1$^+$). Hplc (Magellan C8, Gradient 3, water/acetonitrile/TFA) rt 11.47 min.

Example 42

1-Aminoisoquinolin-7-oyl-D-phenylglycine-4-(3-methylphenyl) piperazinanide 1H nmr (CD$_3$CN) 8.80 (1H,s); 8.25 (1H,d); 7.95 (1H, d); 7.55 (3H, m); 7.45 (3H, m); 7.25 (2H, m); 6.95 (3H, m); 6.15 (1H, s); 3.95 (1H, m); 3.75 (2H,m); 3.65 (1H,m); 3.30 (2H,m); 3.15 (1H,m); 2.60 (1H,m); 2.30 (3H,s). MS TOF 480 (M+1$^+$). Hplc (Magellan C8, Gradient 3, water/acetonitrile/TFA) rt 10.20 min.

Example 43

1-Aminoisoquinolin-7-oyl-D-phenylglycine-4-(3-methoxyphenyl) piperazinamide 1H nmr (CD$_3$CN) 8.80 (1H,s); 8.20 (1H,d); 7.85 (1H, d); 7.45 (1H,d); 7.40 (2H, m); 7.25 (3H, m); 7.05 (1H,d); 6.95 (1H,m); 6.35 (1H,d); 6.30 (2H, m); 6.10 (1H, s); 3.80 (1H, m); 3.60 (2H,m); 3.55 (3H,s); 3.45 (1H,m); 3.05 (2H,m); 2.85 (1H,m); 2.45 (1H,m). MS TOF 496 (M+1$^+$). Hplc (Magellan C8, Gradient 3, water/acetonitrile/TFA) rt 10.85 min.

Example 44

1-Aminoisoquinolin-7-oyl-D-phenylglycine-4-(2-fluorophenyl) piperazinamide 1H nmr (CD$_3$CN) 8.80 (1H,s); 8.25 (1H,d); 7.95 (1H, d); 7.50 (6H, m);7.20 (2H,d); 7.00 (4H,m); 6.15 (1H, s); 3.05 (6H,m); 2.45 (1H,m); 2.15 (1H,m). MS TOF 484 (M+1$^+$). Hplc (Magellan C8, Gradient 3, water/acetonitrile/TFA) rt 11.06 min.

Example 45

1-Aminoisoquinolin-7-oyl-D-phenylglycine-4-(2-hydroxyphenyl) piperazinamide 1H nmr (CD$_3$CN) 8.85 (1H,s); 8.25 (1H,d); 7.95 (1H, d); 7.50 (6H, m); 7.25 (3H,m); 7.00 (2H,m); 6.15 (1H, s); 4.00 (1H,m); 3.80 (2H,m); 3.70 (1H,m); 3.35 (3H,m); 2.80 (1H, m). MS TOF 482 (M+1$^+$). Hplc (Magellan C8, Gradient 3, water/acetonitrile/TFA) rt 8.44 min.

Example 46

1-Aminoisoquinolin-7-oyl-D-phenylglycine-4-(2,4-difluorophenyl) piperazinamide 1H nmr (CD$_3$CN) 8.85 (1H,s); 8.25 (1H,d); 7.95 (1H, d); 7.50 (6H, m); 7.25 (1H,d); 6.95 (3H,m); 6.15 (1H, s); 3.85 (1H,m); 3.65 (2H,m); 3.50 (1H,m); 2.95 (3H,m); 2.40 (1H, m). MS TOF 502 (M+1$^+$). Hplc (Magellan C8, Gradient 3, water/acetonitrile/TFA) rt 11.27 min.

Example 47

1-Aminoisoquinolin-7-oyl-D-phenylglycine-4-(2,3-dimethylphenyl) piperazinamide 1H nmr (CD$_3$OH) 8.60 (1H,s); 8.05 (1H,d); 7.65 (1H, d); 7.20 (6H, m); 6.95 (1H,d); 6.65 (1H,m); 6.55 (1H,d); 6.45 (1H,d); 5.95 (1H, s); 3.60 (1H,m); 3.50 (2H,m); 3.30 (1H, m); 2.55 (3H,m); 2.10 (1H,m) 1.90 (6H,d). MS TOF 494 (M+1$^+$). Hplc (Magellan C8, Gradient 3, water/acetonitrile/TFA) rt 11.98 min.

Example 48

1-Aminoisoquinolin-7-oyl-D-phenylglycine-4-(2,4-dimethylphenyl) piperazinamide 1H nmr (CD$_3$OH) 8.65 (1H,s); 8.05 (1H,d); 7.65 (1H, d); 7.35 (1H,d); 7.20 (5H, m); 6.95 (1H,d); 6.65 (1H,s); 6.60 (1H,d); 6.50 (1H,d); 5.95 (1H, s); 3.60 (1H,m); 3.50 (2H,m); 3.30 (1H,m); 2.55 (3H,m); 2.10 (1H,m) 1.90 (6H,d). MS TOF 494 (M+1$^+$). Hplc (Magellan C8, Gradient 3, water/acetonitrile/TFA) rt 12.00 min.

Example 49

1-Aminoisoquinolin-7-oyl-D-phenylglycine-4-(2,6-dimethylphenyl) piperazinamide 1H nmr (CD$_3$OH) 8.70 (1H,s); 8.10 (1H,d); 7.85 (1H, d); 7.30 (3H,m); 7.20 (3H, m); 7.00 (1H,d); 6.65 (3H,m); 5.95 (1H, s); 3.85 (1H,m); 3.40 (3H,m); 2.800 (2H,m); 2.65 (1H,m); 2.30 (1H,m) 2.10 (3H,s); 1.90 (3H,s). MS TOF 494 (M+1$^+$). Hplc (Magellan C8, Gradient 3, water/acetonitrile/TFA) rt 12.04 min.

Example 50

1-Aminoisoquinolin-7-oyl-D-phenylglycine-4-(2,5-dimethylphenyl) piperazinamide 1H nmr (CD$_3$OH) 8.65 (1H,s); 8.05 (1H,d); 7.65 (1H, d); 7.35 (1H,d); 7.25 (2H, m); 7.15 (3H,m); 6.95 (1H,d); 6.70 (1H,d); 6.50 (1H,d); 6.45 (1H,s); 5.95 (1H, s); 3.60 (1H,m); 3.50 (2H,m); 3.30 (1H,m); 2.55 (3H,m); 2.10 (1H,m) 1.95 (6H,d). MS TOF 494 (M+1$^+$). Hplc (Magellan C8, Gradient 3, water/acetonitrile/TFA) rt 12.09 min.

Example 51

1-Aminoisoquinolin-7-oyl-D-cyclohexylglycine-4-(4'-pyridyl) piperazinamide 1H nmr (DMSO) 9.05 (1H,s); 8–35(1H,d); 8.25 (2H,d); 8.05 (1H,d); 7.75 (1H,d); 7.25 (1H, d); 7.15 (2H,d); 4.80 (1H, m); 4.10–3.50 (broad 8H,m, obscured by solvent); 1.95 (2H,m); 1.70 (4H,m); 1.20 (5H,m). MS TOF 473 (M+1+). Hplc (Magellan C8, Gradient 3, water/acetonitrile/TFA) rt 8.00 min.

Example 52

1-Aminoisoquinolin-7-oyl-D-phenylglycine-4-phenyl piperidinamide 1H nmr (CD$_3$CN) 8.90 (1H,s); 8.35 (1H,d); 8.05 (1H, d); 7.70–7.20 (11H, m); 7.10 (1H, d); 6.20 (1H, s); 4.70 (1H, m); 3.30 (1H,m); 2.80 (2H,m); 1.80 (2H,m); 1.50 (2H,m);

0.50 (H, m). MS TOF 465 (M+1+). Hplc (Magellan C8, Gradient 3, water/acetonitrile/TFA) rt 11.77 min.

Example 53

1-Aminoisoquinolin-7-oyl-D-phenylglycine-4-benzyl piperidinamide 1H nmr (CD$_3$CN) mixture of rotomers 8.65 (1H,d); 8.25 (1H,m); 7.80 (1H, m); 7.55–7.00 (12H, m); 6.10 (1H, m); 4.50 (1H, m); 3.90 (1H,m); 2.80 (4H,m); 1.60 (2H,m); 1.25 (2H,m); 1.00 (1H,m); 0.25 (1H,m); MS TOF 479 (M+1+). Hplc (Magellan C8, Gradient 3, water/acetonitrile/TFA) rt 12.66 min.

Example 54

1-Aminoisoquinolin-7-oyl-D-phenylglycine-4-piperidinopiperidinamide 1H nmr (CD$_3$CN) mixture of conformers 8.70 (1H,d); 8.25(1H,m); 8.10 (1H,m); 7.75 (1H,m); 7.45 (5H,m); 7.05 (1H, d); 6.10 (1H, mn); 4.70 (1H,m); 4.10 (1H,m); 3.50–3.00 (broad 3H,m); 3.00–2.30 (broad 7H,m); 2.10 (1H,m); 1.80 (5H,m); 1.40 (1H,m). MS TOF 472(M+1+). Hplc (Magellan C8, Gradient 2, water/acetonitrile/TFA) rt 12.09 min.

Example 55

1-Aminoisoquinolin-7-oyl-D-cyclohexylglycine-1-S-cyclohexylethylamide 1H nmr (DMSO) 9.05 (1H,s); 8.35 (1H,d); 8.05 (1H,d); 7.75 (1H,d); 7.25 (1H, d); 4.40 (1H, m); 3.65 (1H,m); 1.85–1.50 (broad 11H,m); 1.35–0.80 (broad 11H,m); 1.05 (3H,d); MS TOF 423 (M+1+). Hplc (Magellan C8, Gradient 3, water/acetonitrile/TFA) rt 11.68 min.

Method 5

By solid phase: Typically a Wang resin modified with a 4-nitrophenylcarbonate (see Kim, S. W., et al.Bioorg. Med. Chem. Lett. 8 (1998) 735–738) is reacted with 4,4 bipiperidine The resin was further modified by the attachment of acids. Activation of Fmoc protected amino acid (2–5 eq) was by TBTU/DIPEA, all couplings (minimum 120 min.) were carried out in DMF. Deprotection of the Fmoc group was achieved with 20% piperidine in DMF. Other acid substituents were added as the HOBt or HOAt esters either by activation with HBTU/HATU or DIPCI with or without Boc protection of amino groups. Cleavage of the products from the resin was by treatment (30 min., ambient) with 10% triethylsilane in TFA, filtration, evaporation and trituration with diethylether.

Example 56

1-Aminoisoquinolin-7-oyl-D-phenylglycine-4,4-bipiperidinamide

Wang resin (1 g, 1 mmol./g) was swollen with dry DCM (25 ml.) to this NMM (0.6 ml., 5.6 mmol.) and 4-nitrophenylchloroformate (400 mg., 2 mmol.) was added. The resin was agitated overnight then washed with DCM (25 ml, x6) and DMF (25 ml., x6). 4,4' Bipiperidine (332 mg, 2 mmol.) in DMF (20 ml.) was then added and the resin agitated overnight. The resin was then washed with DMF (25 ml., x6), DCM (25 ml., x6) and diethyl ether (25 ml., x3) then air dried.

The above modified resin (100 mg., 0.1 mmol.) was treated with Fmoc-D-Phenylglycine (0.5 mmol, 187 mg ), DMF(2.5 ml), TBTU in DMF(1.25 ml of a 450 mM solution) and DIPEA in DMF (1.25 ml of a 900 mM solution). The mixture was agitated with nitrogen for 2 hours. Deprotection and washing as Method 1.

A solution of 1-aminoisoquinoline-7-carboxylic acid trifluoroacetic acid salt (150 mg 0.5 mmole ) (Example 88) in dry dimethylformamide (DMF) was treated successively with HOAt (102 mg 0.75 mmole ) and EDC (115 mg 0.6 mmole ) and stirred at room temperature for 10 min. The mixture was transferred to the reaction vessel on the Symphony and agitated for 10 hours with nitrogen. The resin was washed with DMF (6x5 ml), DCM (6x5 ml) and air dried. The product was cleaved from the resin with 10% triethylsilane in TFA (10 ml) for 30 minutes, the resin filtered off and the TFA solution evaporated to dryness and triturated with diethyl ether to give the crude product. The crude product was dissolved in water (10 ml), filtered and purified by preparative reverse phase Hplc.

1H nmr (DMSO) 8.80 (1H,s); 8.15 (1H,d); 7.70 (1H,d); 7.50 (1H,d); 7.25 (2H,m); 7.10 (3H, m); 7.00 (1H,d); 5.90 (1H, s); 4.30 (1H,m); 3.80 (1H,m); 3.3–2.3 (8H, various m, obscured by solvent); 1.80–0.50 (8H, various m). MS TOF 472 (M+1+). Hplc (Magellan C8, Gradient 1, water/acetonitrile/TFA) rt 7.32 min.

Other compounds made by the above method:

Example 57

1-Aminoisoquinolin-7-oyl-D,L-2-thienylglycine-4,4-bipiperidinamide

MS TOF 478 (M+1+). Hplc (Magellan C8, Gradient 3, water/acetonitrile/TFA) rt 10.43 min.

Example 58

1-Aminoisoquinolin-7-oyl-D,L-1-naphthylglycine-4,4-bipiperidinamide

MS TOF 522 (M+1+). Hplc (Magellan C8, Gradient 3, water/acetonitrile/TFA) rt 12.99 min.

Example 59

1-Aminoisoquinolin-7-oyl-D-cyclohexylglycine-4,4-bipiperidinamide

MS TOF 478 (M+1+). Hplc (Magellan C8, Gradient 3, water/acetonitrile/TFA) rt 12.65 min.

Example 60

1-Aminoisoquinolin-7-oyl-L-phenylglycine-4,4-bipiperidinamide

MS TOF 472 (M+1+). Hplc (Magellan C8, Gradient 3, water/acetonitrile/TFA) rt 10.89 min.

Example 61

1-Aminoisoquinolin-7-oyl-D,L-3-chlorophenylglycine-4,4-bipiperidinamide

MS TOF 507 (M+1+). Hplc (Magellan C8, Gradient 3, water/acetonitrile/TFA) rt 12.54 min.

Example 62

1-Aminoisoquinolin-7-oyl-D-isoleucine-4,4-bipiperidinamide

MS TOF 452 (M+1+). Hplc (Magellan C8, Gradient 3, water/acetonitrile/TFA) rt 11.04 min.

Method 6

Typically Boc-(R)-1,2 diamino-1-phenylethane was prepared by the method of O'Brien, P. et al. J. Med. Chem. 37 (1994) 12, 1810–1822. The free amino group was reacted with an acid chloride or an activated acid, all couplings (minimum 120 min.) were carried out in DMF. After an aqueous work up the deprotection of the Boc group was achieved with TFA. Other acid substituents were added as the HOBt or HOAt esters either by activation with HBTU/HATU, EDC or DIPCI with or without Boc protection of amino groups. The final products were purified by preparative reverse phase Hplc.

Example 63

2(R)-{[N-(1-Aminoisoquinoline)-7-oyl]amino}-2-phenylethyl-4-methylbenzamide

Boc-(R)-1,2 diamino-1-phenylethane (2 g) was dissolved in DCM (80 ml) and toluoylchloride (1.2 ml.) and TEA (1.1 ml.) added. The mixture was stirred at room temperature under argon overnight. The mixture was then washed with 2M sodium hydroxide solution, water, 5% hydrochloric acid and brine, dried over magnesium sulphate, filtered and evaporated. The product was recrystallised from hexane dissolved in DCM (50 ml.) and treated with TFA for 2 hrs. The solvent was evaporated and the solid triturated with diethylether.

A solution of 1-aminoisoquinoline-7-carboxylic acid trifluoroacetic acid salt (300 mg 1 mmole) in dry DMF (10 ml.) was treated successively with HOAt (204 mg 1.5 mmole) and EDC (230 mg 1.2 mmole) and stirred at room temperature for 10 min. The mixture was added to the R-Amino-2-phenylethyl-4-methylbenzamide. TFA salt (0.38 g, 1.03 mmol.) with DIPEA (129 mg, 1 mmol.) and stirred overnight. After aqueous work up the final products were purified by preparative reverse phase Hplc.

1H nmr (DMSO) 8.90 (1H,s); 8.35 (1H,d); 7.95 (1H,d); 7.65 (1H,d); 7.60 (2H,d); 7.55 (1H,d); 7.25 (6H,m); 5.35 (1H, m); 3.65 (2H,m); 2.25 (3H,s). MS TOF 425 (M+1+). Hplc (Magellan C8, Gradient 3, water/acetonitrile/TFA) rt 10.88 min.

Other compounds made by the above method:

Example 64

2(R)-{[N-(1-Aminoisoquinoline)-7-oyl]amino}-2-phenylethyl-4-methoxybenzamide 1H nmr (DMSO) 9.00 (1H,s); 8.50 (1H,d); 8.20 (1H, d); 7.85 (3H,m); 7.60 (1H,d); 7.45 (5H,m); 7.15 (2H,d); 5.55 (1H, m); 3.95 (3H,s); 3.85 (2H,m). MS TOF 441 (M+1+). Hplc (Magellan C8, Gradient 3, water/acetonitrile/TFA) rt 10.90 min.

Example 65

2(R)-{[N-(1-Aminoisoquinoline)-7-oyl]amino}-2-phenylethyl benzamide 1H nmr (CD$_3$OD) 8.75 (1H,s); 8.25 (1H,d); 7.85 (1H,d); 7.60 (2H,d); 7.55 (1H,d); 7.30 (9H,m); 5.35 (1H, m); 3.85 (2H,m). MS TOF 410 (M+1+). Hplc (Magellan C8, Gradient 3, water/acetonitrile/TFA) rt 10.26 min.

Example 66

2(R)-{[N-(1-Aminoisoquinoline)-7-oyl]amino}-2-phenylethyl benzylamide 1H nmr (CD$_3$OD) 8.65 (1H,s); 8.10 (1H,d); 7.80 (1H,d); 7.55 (1H,d); 7.55 (1H,d); 7.25 (7H,m); 7.05 (1H,d); 6.95 (3H,m); 5.25 (1H, m); 4.15 (1H,d); 3.75 (2H,m). MS TOF 424 (M+1+). Hplc (Magellan C8, Gradient 3, water/acetonitrile/TFA) rt 10.13 min.

Example 67

2(R)-{[N-(1-Aminoisoquinoline)-7-oyl]amino}-2-phenylethyl benzosulphonamide 1H nmr (CD$_3$OD) 8.55 (1H,s); 7.95 (1H,d); 7.70 (4H,m); 7.45 (3H,m); 7.20 (5H,m); 6.90 (1H,d); 5.10 (1H, m); 3.30 (2H,m). MS TOF 447 (M+1+). Hplc (Magellan C8, Gradient 3, water/acetonitrile/TFA) rt 11.22 min.

Example 68

2(R)-{[N-(1-Aminoisoquinoline)-7-oyl]amino}-2-phenylethyl cyclohexanecarboxamide 1H nmr (CD$_3$OD) 8.55 (1H,s); 7.95 (1H,d); 7.70 (2H,m); 7.25 (5H,m); 6.95 (1H,d); 5.20 (1H, m); 3.50 (2H,m) 2.05 (1H,m); 1.6–1.0 (10H, broad m). MS TOF 417 (M+1+). Hplc (Magellan C8, Gradient 3, water/acetonitrile/TFA) rt 11.29 min.

Example 69

2(R)-{[N-(1-Aminoisoquinoline)-7-oyl]amino}-2-phenylethyl cyclohexyl acetamide 1H nmr (CD$_3$OD) 8.55 (1H,s); 7.95 (1H,d); 7.70 (2H,m); 7.25 (5H,m); 6.95 (1H,d); 5.20 (1H, m); 3.55 (2H,m) 2.00 (2H,m); 1.7–0.6 (11H, broad m). MS TOF 431 (M+1+). Hplc (Magellan C8, Gradient 3, water/acetonitrile/TFA) rt 11.49 min.

Method 7

Typically 4,4'-Bipiperidine was mono protected with the tert-butyl oxy carbonyl (Boc) group. The free amino group was reacted with an alkylating agent. After an aqueous work up the deprotection of the Boc group was achieved with TFA. Other acid substituents were added as the HOBt or HOAt esters either by activation with HBTU/HATU, EDC or DIPCI with or without Boc protection of amino groups. The final products were purified by preparative reverse phase Hplc.

t-Butyl 4-(piperidin-4-yl)piperidine-1-carboxylate 4,4'-Bipiperidine dihydrochloride (5 g, 20.7 mmol) was dissolved in NaOH (30 ml, 2N) and ethanol (50 ml). To this solution was added Di-tert-butyl dicarbonate (4.52 g, 20.7 mmol) and the reaction mixture left to stir overnight. The ethanol was removed under vacuo and the basic layer extracted with ethyl acetate (100 ml) to remove any DiBoc material. The desired product was then extracted into aq. 5% HCl and the pH adjusted to 11. Extraction with ethyl acetate (100 ml), washing with brine and drying gave the title compound as a white solid.

Example 70

1-Aminoisoquinolin-7-oyl-D-phenylglycine-4,4'-(1'-ethoxycarbonymethyl)bipiperidinamide To a suspension of t-Butyl 4-(piperidin-4-yl)piperidine-1-carboxylate (536 mg, 2 mmol), and potassium carbonate (580 mg, 4.2 mmol) in acetone (25 mL) was added ethyl bromoacetate (248 μL, 2.2 mmol) and the reaction mixture left to stir at room temperature overnight. The acetone was removed and the residue treated with ethyl acetate, washed with water, dried with magnesium sulphate, filtered and evaporated. The product was further elaborated as Method 4 after the removal of the Boc protecting group.

1H nmr (CD$_3$CN) 8.55 (1H,s); 8.15 (1H,d); 8.05 (1H,d); 7.65 (1H,d); 7.35 (2H,m); 7.20 (3H, m); 7.00 (1H,d); 5.90 (1H, s); 4.45 (1H,m); 4.10 (2H,m); 3.80 (1H,m); 3.70 (2H,m); 3.3–2.3 (8H, various m, obscured by solvent); 1.70–0.70 (8H, various m); 1.10 (3H,t). MS TOF 558 (M+1$^+$). Hplc (Magellan C8, Gradient 3, water/acetonitrile/TFA) rt 8.49 min.

Other compounds made by the above method:

Example 71

1-Aminoisoquinolin-7-oyl-D-phenylglycine-4,4'-(1'-ethyl)bipiperidinamide 1H nmr (CD$_3$OH) 8.75 (1H,s); 8.15 (1H,d); 7.75 (1H,d); 7.45 (1H,d); 7.25 (5H,m); 7.05 (1H,d); 5.95 (1H, s); 4.45 (1H,m); 3.80 (1H,m); 3.70 (2H,m); 3.35 (2H,m); 2.90 (2H, m); 2.60 (4H,m); 1.85 (1H,m); 1.65 (2H,m); 1.40–0.70 (7H, various m); 1.10 (3H,t). MS TOF 500 (M+1$^+$). Hplc (Magellan C8, Gradient 3, water/acetonitrile/TFA) rt 7.93 min.

Example 72

1-Aminoisoquinolin-7-oyl-D-phenylglycine-4,4'-(1'-propyl)bipiperidinamide 1H nmr (CD$_3$OH) 8.60 (1H,s); 8.05 (1H,d); 7.80 (1H,d); 7.45 (1H,d); 7.35 (5H,m); 7.10 (1H,d); 5.95 (1H, s); 4.35 (1H,m); 3.85 (1H,m); 3.40 (3H,m); 3.05–2.55 (broad 6H,m); 1.90 (1H,m); 1.60 (5H,m); 1.25 (4H,m); 0.80 (4H,m). MS TOF 514 (M+1$^+$). Hplc (Magellan C8, Gradient 3, water/acetonitrile/TFA) rt 8.20 min.

Example 73

1-Aminoisoquinolin-7-oyl-D-phenylglycine-4,4'-(1'-carboxymethyl)bipiperidinamide 1-Aminoisoquin-7-oyl-D-phenylglycine-4,4'-(1'-ethoxycarbonylmethyl)bipiperidinamide (40 mg, 0.05 mmol) was treated with sodium hydroxide 2N (100 µL, 4 eq.)in ethanol (5 mL) overnight. Purification by preparative HPLC gave the title compound as a white solid.

1H nmr (CD$_3$CN) 8.80 (1H,s); 8.35 (1H,d); 8.15 (1H,d); 7.70 (1H,d); 7.35 (2H,m); 7.20 (3H, m); 6.95 (1H,d); 5.90 (1H, s); 4.45 (1H,m); 3.80 (1H,m); 3.65 (2H,m); 3.40 (2H,m); 3.00–2.30 (5H, vaious m); 1.70–0.70 (9H, various m). MS TOF 530 (M+1$^+$). Hplc (Magellan C8, Gradient 3, water/acetonitrile/TFA) rt 7.88 min.

Example 74

1-Aminoisoquinolin-7-oyl-D-phenylglycine-4,4'-(1'-amidomethyl)bipiperidinamide

1-Aminoisoquin-7-oyl-D-phenylglycine-4,4'-(1'-ethoxymethyl)bipiperidinamide (40 mg, 0.05 mmol) was treated with excess ammonia gas in anhydrous ethanol (5 mL) for 5 days. Purification by preparative HPLC gave the title compound as a white solid.

1H nmr (CD$_3$CN) 8.65 (1H,s); 8.15 (1H,d); 7.75 (1H,d); 7.40 (3H,m); 7.25 (3H, m); 7.05 (1H,d); 5.95 (1H, s); 4.45 (1H,m); 3.90 (1H,m); 3.65 (2H,m); 3.35 (2H,m); 3.00–0.80 (14H, vaious m, obscured by solvent). MS TOF 529 (M+1$^+$). Hplc (Magellan C8, Gradient 3, water/acetonitrile/TFA) rt 7.73 min.

Example 75

1-Aminoisoquinolin-7-oyl-D-phenylglycine-4,4'-(1'-methyl)bipiperidinamide

CBz-D-phenylglycine-4-[1-(Boc)piperidin-4-yl] piperidinamide

To a solution of CBz-D-phenylglycine (877 mg, 3.1 mmol) in anhydrous THF (40 ml) at −25° C. was added N-methylmorpholine (336 µl, 3.1 mmol) and isobutyl chloroformate (419 µl, 3.1 mmol). The resulting suspension was left to stir for 5 min at this temperature and then the t-Butyl 4-(piperidin-4-yl)piperidine-1-carboxylate (825 mg, 3.1 mmol) in anhydrous THF (5 ml) was added in one portion at −25° C. and the reaction mixture allowed to warm to room temperature over 1 hour. The N-methylmorpholine hydrochloride was filtered off and the THF removed under vacuo. The resulting solid was treated with TFA/DCM (20 ml, 1:1) and the reaction mixture left to stir for 2 hours. The organics were removed under vacuo, the residue dissolved in ethyl acetate (100 ml), washed with aq. sodium bicarbonate solution, brine, dried and concentrated to yield the title compound as a clear oil (1.12 g, 84% over two steps).

CBz-D-phenylglycine-4-(1-methylpiperidin-4-yl) piperidinamide

To a solution of CBz-D-phenylglycine-4-[1-(Boc) piperidin-4-yl]piperidinamide (1.1 g, 2.5 mmol) in acetonitrile (40 ml) and aq. formaldehyde (10 ml) was added sodium cyanoborohydride (315 mg, 5 mmol) portionwise over 10 min. The reaction mixture was left to stir for 3 hours and then poured onto water (50 ml), containing conc ammonia solution (5 ml) and left to stir for 15 min. Extraction with ethyl acetate (100 ml), washing with brine and drying gave the title compound as a colourless oil (1.1 g, 97%).

D-Phenylglycine-4-(1-methylpiperidin-4-yl) piperidinamide

A vigorously stirred solution of CBz-D-phenylglycine-4-(1-methylpiperidin-4-yl)piperidinamide (1.1 g, 2.45 mmol) in methanol (120 ml), containing Palladium on carbon (200 mg ) was treated with hydrogen gas (balloon) at atmospheric pressure overnight. The reaction mixture was filtered through celite and concentrated to yield the title compound as a colourless oil (585 mg, 76%).

The resultant product was coupled to 1-amino-isoquinoline carboxylic acid (TFA salt) using method 4.

1H nmr (CD$_3$CN) 8.60 (1H,s); 8.10 (1H,d); 7.75 (1H,d); 7.45 (3H,m); 7.25 (3H, m); 7.00 (1H,d); 5.90 (1H, s); 4.30 (1H,m); 3.80 (1H,m); 3.3–2.3 (8H, various m, obscured by solvent); 2.50 (3H,s); 1.80–0.50 (8H, various m). MS TOF 486 (M+1$^+$). Hplc (Magellan C8, Gradient 3, water/acetonitrile/TFA) rt 9.11 min.

Example 76

2(R)-{[N-(1-Aminoisoquinoline)-7-oyl]amino}-2-phenylethyl-4-methylphenylcarbamate To a solution of Boc-(R)-phenylglycinol (500 mg 3.65 mmole) in DMF (20 ml) was added 4-methylphenylisocyanate (0.5 ml 4.0 mmole) and the mixture warmed to 50° C. before standing at room temperature overnight. Dilution with ethyl acetate and washing with sat. sodium bicarbonate gave after drying (magnesium sulphate) and evaporation of solvent the crude intermediate which was purified by flash chromatography (silica gel, EtOAC 0–20% in DCM)

Deprotection of the amine was carried out using 50% TFA in DCM (30 min), evaporation of solvent under reduced pressure, dissolving in DCM, washing with sat sod. bicarbonate, drying (magnesium sulphate) and evaporation.

Coupling of the intermediate to 1-amino-isoquinoline carboxylic acid (TFA salt) was carried out using the standard method 4.

1H nmr (DMSO) 9.05 (1H,s); 8.40 (1H,d); 8.05 (1H,d); 7.70 (1H,d); 7.55–7.20 (7H,m); 7.05 (3H,m); 5.55 (1H, m); 4.35 (2H,d); 2.25 (3H,s). MS TOP 441 (M+1+). Hplc (Magellan C8, Gradient 3, water/acetonitrile/TFA) rt 11.60 min.

Example 77

1-Aminoisoquinolin-7-oyl-D-phenylglycine-2-(4-aminophenoxy)cyclopentyl amide

Cyclopentene oxide (5 g) was dissolved in ethanol (100 ml) and water (25 ml) and treated with sodium azide (3.9 g) and ammonium chloride (3.2 g) at reflux for 8 h. the mixture was cooled, excess solvent evaporated off at reduced pressure and extracted with ether. The organic solution was washed with water, dried (MgSO$_4$) and evaporated. The residues were taken up in hexane, washed with water to remove any remaining ethanol, dried (MgSO4) and evaporated to give trans-1-azidocyclopentan-2-ol 3.6 g.

Trans-1-azidocyclopentan-2-ol 1.27 g was dissolved in DMF and treated with sodium hydride (400 mg. 60%) at room temperature for 1h. 4-Fluoronitrobenzene (1.41 g) was added and the mixture stirred at 50° C. for 4 h and then left at room temperature overnight. The reaction was quenched with water and extracted with ether. The organic solution was washed with water, dried (MgSO$_4$) and evaporated. Purification by flash chromatography (SiO2-20% DCM/hexane) gave trans-2-(4-nitrophenoxy) cyclopentylazide. $^1$H nmr (CDCl$_3$) 8.22 (2H, d); 6.98 (2H, d); 5.63 (1H, m); 4.07 (1H, m); 2.20 (2H, m); 1.87 (4H, m).

Hydrogenation in ethanol (30 ml) using 5%Pd on C (100 mg) gave cis-2-(4-aminophenoxy)cyclopentylamine.

Trans-2-(4-aminophenoxy)cyclopentylamine was coupled to Boc-D-phenylglycine using TBTU/DIPEA/DMF as method 4, the resultant product was deprotected (TFA/DCM) and coupled to 1-amino-isoquinoline carboxylic acid (TFA salt) using method 4.

$^1$H nmr (CD$_3$CN) 8.55 (1H,s); 8.10 (1H,d); 7.70 (1H,d); 7.35 (1H,d); 7.25 (5H, m); 7.00 (1H, d); 6.55 (4H,s); 5.40 (1H, s); 4.30 (1H,m); 4.00 (1H,m); 2.00–100 (broad 6H, m). MS TOF 496 (M+1$^+$). Hplc (Magellan C8, Gradient 3, water/acetonitrile/TFA) rt 9.26 min.

Example 78

1-Aminoisoquinolin-7-oyl-D-phenylglycinyl-cis-4-phenoxyproline t-Butyldicarbonate (1.1 g) and then sat. sodium bicarbonate (20 ml) were added to a suspension of trans-Hyp-OBn (1.1 g) in THF (25 ml) and the mixture stirred for 30 min. The mixture was diluted with ethyl acetate and washed with water, dried (MgSO$_4$) and evaporated. Flash chromatography (SiO2 DCM then ether) gave Boc-Hyp-OBn 1.18 g DEAD (diethyl azadicarboxylate) (0.59 ml) was added to a mixture of Boc-Hyp-OBn (1.1 g), triphenylphosphine (0.9 g) and phenol (0.32 g) in THF 10 ml over 30 min. The mixture was stirred overnight and triphenylphosphine (0.45 g), phenol (0.16 g) and DEAD (0.3 ml) were added and the mixture stirred overnight before concentration. The residue was taken up in ethyl acetate and washed with 2M sodium hydroxide, saturated sodium bicarbonate, dried (MgSO4) and evaporated. Flash chromatography (SiO2 hexane then 20% ethylacetate in hexane) gave Boc-cis-4-phenoxyproline benzyl ester 496 mg.

Boc-cis-4-phenoxyproline benzyl ester was deprotected (TFA/DCM) and coupled to Boc-D-phenylglycine which was deprotected (TFA/DCM) and coupled to 1-aminoisoquinoline-7-carboxylic acid (TFA salt) as method 4. The product was hydrogenated in ethanol (5% Pd on C, atmospheric pressure) for 4 h. to give the title compound.

$^1$H nmr (CD$_3$CN) 9.05 (1H,s); 8.35 (1H,d); 8.00 (1H,d); 7.70 (1H,d); 7.55 (1H,d); 7.35 (7H, m); 7.00 (1H, m); 6.85 (2H,d); 6.00 (1H, s); 5.05 (1H,m); 4.60 (1H,d); 3.80 (1H,m); 3.60 (1H,m); 2.50 (1H,m); 2.25 (1H,m). MS TOF 511 (M+1$^+$). Hplc (Magellan C8, Gradient 3, water/acetonitrile/TFA) rt 10.36 min.

Example 79

1-Aminoisoquinolin-7-oyl-D-phenylglycine-4-(4'-pyrimidyl) piperazinamide

A mixture of Boc-piperazine (2 g), sodium bicarbonate (2 g) and 2,4-dichloro-pyrimidine (1.5 g) in ethanol (40 ml)/water (20 ml) was stirred at room temperature for 1 h. Ethyl acetate (200 ml) was added and the mixture washed twice with water, dried (MgSO$_4$) and evaporated. The product was crysrallised from DCM/ether, 252 g.

The above product (1 g) was dissolved in ethanol (30 ml) and hydrogenated (5% Pd on C, 50 psi) for 4 h. to give Boc-4-(4'-pyrimidyl)-piperazine. $^1$H nmr (CDCl$_3$) 8.53 (1H, s); 8.41 (1H, d); 6.42 (1H, d); 3.45 (8H, m); 1.35 (9H, s).

Boc-4-(4'-pyrimidyl)-piperazine was deprotected (TFA/DCM) and coupled to Boc-D-phenylglycine using method 4 to give Boc-D-phenylglycine-4-(4'-pyrimidyl)-piperazinamide which was deprotected (TFA/DCM) and coupled to 1-aminoisoquinoline-7-carboxylic acid (TFA salt) using method 4.

$^1$H nmr (CD$_3$CN) 9.00 (1H,s); 8.75 (1H,s); 8.30 (1H,d); 8.20 (1H,d); 7.95 (1H, d); 7.70 (1H, d); 7.50 (2H, m); 7.35 (3H, m); 7.25 (1H,d); 7.10 (1H,d); 6.15 (1H, s); 3.70–3.30 (broad 8H,m). MS TOF 468 (M+1$^+$). Hplc (Magellan C8, Gradient 1, water/acetonitrile/TFA) rt 9.09 min.

Example 80

(R)-1-(2-{1-Aminoisoquinolin-7-oyl}amino-2-phenylethyl)piperidin-2-one (R)-1-(2-Butoxycarbonylamino-2-phenylethyl) piperidin-2-one Boc-(R)-1,2 diamino-1-phenylethane (prepared by the method of O'Brien, P. et al. J. Med. Chem. 37 (1994) 12, 1810–1822) (0.3 g, 1.27 mmol.), methyl-5-bromovalerate (0.18 ml., 1.27 mmol.) and DBU (0.19 ml) were dissolved in absolute ethanol(10 ml.) and stirred under reflux for 3 days. The ethanol was removed by evaporation and the residue taken up into ethylacetate, washed with 10% hydrochloric acid and brine, dried over magnesium sulphate, filtered and evaporated to give the product. The above product was further elaborated by Method 4 to the title compound.

1H nmr (CD$_3$OD) 8.80 (1H,s); 8.20 (1H,d); 7.85 (1H, d); 7.55 (1H, d); 7.25 (6H, m); 5.45 (1H, m); 4.10 (2H,m); 3.40 (2H,m); 2.70 (4H,m); 2.25 (2H,m). MS TOF 389 (M+1$^+$). Hplc (Magellan C8, Gradient 3, water/acetonitrile/TFA) rt 9.58 min.

Example 81

(R)-1-(2-{1-Aminoisoquinolin-7-oyl}amino-2-phenylethyl)-1,2 dihydro-1-oxo isoquinoline (R)-1-(2-Butoxycarbonylamino-2-phenylethyl)-1,2 dihydro-1-oxo isoquinoline Boc-(R)-1,2 diamino-1-phenylethane (prepared by the method of O'Brien, P. et al. J. Med. Chem. 37 (1994) 12, 1810–1822) (0.82 g) was dissolved in toluene (50 ml.). Homophthalic anhydride (2.2 g) was added followed by TEA (1.8 ml.). The mixture was heated to 120° C. under nitrogen overnight. The reaction mixture was allowed to cool and washed with 2M sodium hydroxide solution, 10% hydrochloric acid and brine, dried over magnesium sulphate, filtered and evaporated. The residue was dissolved in methanol (17.5 ml.) and DCM (35 ml.) and sodium borohydride (70 mg. ) added as one portion. The reaction mixture was stirred under argon for 6 days. 50% Hydrochloric acid solution was then added and the reaction stirred for 1 hr. The solvents were then removed under vacuo and the residue taken up into ethylacetate (50 ml.), washed with water and brine, dried over magnesium sulphate, filtered and evaporated to give the product.

The above product was further elaborated by Method 4 to the title compound.

1H nmr (CDCl$_3$) 8.95 (1H,s); 8.40 (1H,d); 8.25 (2H,d); 7.75 (1H, d); 7.60 (1H,m); 7.50 (3H,m); 7.35 (1H, d); 7.20 (5H, m); 6.90 (1H,d); 6.50 (1H,d); 5.45 (1H, m); 4.75 (1H,m); 4.10 (1H,m). MS TOF 435 (M+1$^+$). Hplc (Magellan C8, Gradient 3, water/acetonitrile/TFA) rt 10.10 min.

Example 82

N-{1(R)-Phenyl-2-(N-phthalimido)ethyl}-1-aminoisoquinolin-7-carboxamide (R)-N-(2-Butoxycarbonylamino-2-phenylethyl) phthalimide Boc-(R)-1,2 diamino-1-phenylethane (prepared by the method of O'Brien, P. et al. J. Med. Chem. 37 (1994) 12, 1810–1822) (0.3 g, 1.27 mmol.), phthalic anhydride (0.2 g., 1.4 mmol.) and TEA (0.1 ml) were dissolved in chloroform (20 ml.) and stirred under reflux for 2 days. The reaction mixture was then washed with 10% hydrochloric acid, 2M sodium hydroxide solution and brine, dried over magnesium sulphate, filtered and evaporated to give the product. The above product was further elaborated by Method 4 to the title compound.

1H nmr (CD$_3$OD) 9.00 (1H,s); 8.40 (1H,d); 8.10 (1H, d); 7.90 (4H,m); 7.80 (1H, d); 7.55 (2H,d); 7.35 (4H, m); 5.65 (1H, m); 4.15 (2H,d). MS TOF 437 (M+1$^+$). Hplc (Magellan C8, Gradient 3, water/acetonitrile/TFA) rt 11.19 min.

Example 83

2(R)-{N-(1-Aminoisoquinolin-7-oyl)amino}-2-phenylethyl-4-methylbenzoate

Boc-(R)-Phenylglycinol (2 g, 8.4 mmol.) was dissolved in DCM (50 ml) and toluoylchloride (1.11 ml.) and TEA (1.1 ml.) added. The mixture was stirred at room temperature under argon overnight. The mixture was then washed with 2M sodium hydroxide solution, water, 5% hydrochloric acid and brine, dried over magnesium sulphate, filtered and evaporated. The product was recrystallised from hexane dissolved in DCM (50 ml.) and treated with TFA for 2 hrs. The solvent was evaporated and the solid triturated with diethylether. A solution of 1-aminoisoquinoline-7-carboxylic acid trifluoroacetic acid salt (200 mg 0.66 mmole) in dry DMF (5 ml.) was treated successively with HOAt (140 mg 1 mmole) and EDC (147 mg 0.8 mmole ) and stirred at room temperature for 10 min. The mixture was added to the R-Amino-2-phenylethyl-4-methylbenzoate. TFA salt (0.23 g, 1.03 mmol.) with DBU (0.2 ml) and stirred overnight. After aqueous work up the final products were purified by preparative reverse phase Hplc.

1H nmr (DMSO) 8.90 (1H,s); 8.20 (1H,d); 7.90 (1H,d); 7.65 (2H,d); 7.60 (1H,d); 7.45 (2H,d); 7.20 (6H,m); 5.45 (1H, m); 4.45 (2H,d); 2.25 (3H,s). MS TOF 416 (M+1+). Hplc (Magellan C8, Gradient 3, water/acetonitrile/TFA) rt 11.82 min.

Example 84

O-(1-Aminoisoquinolin-7-oyl)-R-mandelyl-4-methylbenzylamide

R-Mandelic acid (152 mg, 1 mmol.) was dissolved in DMF(3 ml) with HATU (380 mg., 1 mmol.) and DIPEA(350 μl ), 2 mmol.) To this mixture was added 4-methylbenzylamine (121 mg., 1 mmol.) The mixture was stirred overnight. The mixture was then taken up into ethylacetate and washed with water, sodium carbonate solution, water, 10% hydrochloric acid solution and water. The ethylacetate was evaporated. 1-Aminoisoquinoline-7-carboxylic acid (180 mg ), HATU (380 mg, 1 mmol.) and DIPEA (350 μl 1, 2 mmol.) dissolved in DMF (5 ml) and stirred for 10 mins. This mixture was then added to the above product together with DBU (100 μl). The miture was then stirred overnight. The mixture was then taken up into ethylacetate (50 ml) and washed with water, sodium carbonate solution and water. The ethylacetate was then evaporated and the crude product purified by preparative hplc.

1H nmr (CD$_3$CN) 9.10 (1H, s); 8.42 (1H, d); 7.93 (1H, d); 7.65 (2H, d); 7.35 (1H,d); 7.30 (2H, m)); 7.20 (1H,d); 7.00 (4H, m); 6.25 (1H, s); 4.25 (2H, m);2.20 (3H, m). MS TOF 427 (M+1$^+$). Hplc (Jupiter5 C18, Gradient 3, water/acetonitrile/TFA) rt 11.48 min.

Example 85

1-Amino-3,4-dihydroisoquinolin-7-oyl-D-cyclohexylglycine-1-S-cyclohexylethylamide A vigorously stirred solution of 1-Aminoisoquinolin-7-oyl-D-cyclohexylglycine-1-S-cyclohexylethylamide TFA salt (100 mg, 0.40 mmol) (see examples for Method 4) in 50%, 50% HCl/ethanol (10 ml), containing platinum oxide (20 mg ) was treated with hydrogen gas at atmospheric pressure overnight. The reaction mixture was filtered through celite, concentrated and purified by preparative HPLC to yield the title compound as a white solid.

1H nmr (DMSO) 8.40 (1H,s); 8.10(1H,d); 7.55 (1H, d); 4.35 (1H, d); 3.70 (1H,m); 3.60 (2H,m); 3.10 (2H,m); 1.95–1.60 (broad 11H,m); 1.35–0.90 (broad 11H,m); 1.05 (3H,d); MS TOF 425 (M+1+). Hplc (Magellan C8, Gradient 3, water/acetonitrile/TFA) rt 11.42 min.

Example 86

3-([R]-1-phenyl-1-aminomethyl)-5-benzyl-2H-1,2,4-triazole

EDC (1.6 g) was dissolved in DMF (20 ml.) and treated with HOAt (1.16 g) in DMF (10 ml.) and stirred for 10 mins. DIPEA (1.46 ml.) was then added and the stirring continued for a further 15 mins. Boc-D-phenylglycine (2 g) in DMF (10 ml.) was then added dropwise and stirring continued for a further 25 mins. 1M Hydrazine in THF (84 ml.) was then added and the mixture stirred over night. The solvents were then evaporated and the residue treated with water (100 ml.), basified with 2M sodium hydroxide solution and extracted with ethylacetate. The combined extracts were washed with water and brine, dried with magnesium sulphate, filtered and evaporated to give a yellow solid (1.38 g).

1H nmr (CDCl$_3$) 7.20 (5H,s); 5. 55 (1H,s); 1.25 (9H,s)

The above product (0.3 g, 1.13 mmol.) was dissolved in ethanol (6 ml.) and added dropwise to a solution of benzyl ethyl imidate hydrochloride in ethanol (3 ml.) at room temperature. The mixture was stirred for 30 mins.

The solvent was then evaporated and the residue treated with dilute sodium bicarbonate solution and extracted with ethylacetate. The combined extracts were washed with brine, dried over magnesium sulphate, filtered and evaporated to give a yellow gum. (0.43 g).

$^1$H nmr (CDCl$_3$) 7.30 (10H,m); 5.80 (1H,s); 3.50 (2H,m); 1.45 (9H,s).

The above crude product (0.43 g, 1.12 mmol.) was dissolved in xylene (60 ml.) with para toluenesulphonic acid (cat.) and heated to 160° C. for 1 day. The xylene was removed under vacua and the triazole (0.35 g) used without further purification.

1H nmr (CDCl$_3$) 7.20 (10H,m); 5.70 (1H,s); 4.00 (2H,m); 1.30 (9H,s).

Coupling of this triazole intermediate to 1-aminoisoquinoline-7-carboxylic acid can be carried out using the standard method Method 4.

Example 87

2- (1-Phenyl-1-aminomethyl)-4-phenylthiazole

To a solution of Boc-D-phenylglycine (875 mg 3.5 mmole) in a 1:1 mixture of DMF and DCM (40 ml) was added 1-hydroxybenzotriazole (520 mg 1.1 equiv.) and DIPCI (602 µl 1.1 equiv.) and the mixture stirred for 30 min at rt. Ammonia gas was bubbled in and the mixture left overnight before diluting with ethyl acetate and washing with 10% hydrochloric acid and sat. sodium bicarbonate. The organic solution was dried (magnesium sulphate) and evaporated. Flash chromatography (silica gel DCM/ethylacetate 0–50%) gave the amide 770 mg 86%. To a solution of Boc-D-phenylIglycine amide (740 mg 2.96 mmole ) in THF 25 ml was added Laeso'reagent (1.2 g) and the mixture stirred overnight. The solvent was evaporated off under reduced pressure and the residue purified by flash chromatography (silica gel—hexane/ethyl acetate 10 to 30%) to give the thioamide 671 mg.

The thioamide (650 mg ) was dissolved in acetone (20 ml) and phenacyl bromide (486 mg 1 equiv) stirred for 30 min and then diluted with chloroform/aqueous sod. bicarbonate (20 ml each), separated, dried (magnesium sulphate) and evaporated. The residue was dissolved in DCM (20 ml) and treated with pyridine (350 µl) and trifluoroacetic anhydride (360 µl). After 150 min the solvent was removed under reduced pressure and the residues redissolved in DCM and washed with sat. sod. bicarbonate. Purification by flash chromatography (silica gel—hexane/ethyl acetate 10 to 30%) gave the thiazole intermediate 687 mg.

Deprotection of the amine was carried out using 50% TFA in DCM (30 min), evaporation of solvent under reduced pressure, dissolving in DCM, washing with sat sod. bicarbonate, drying (magnesium sulphate) and evaporation to yield the product.

$^1$H nmr (CDCl$_3$) 7.80 (1H,d); 7.25 (10H,m); 5.95 (1H,s).

Coupling of this thiazole intermediate to 1-aminoisoquinoline-7-carboxylic acid can be carried out using the standard method Method 4.

Example 88

1-Aminoisoquinoline-7-carboxylic acid

A 1L flask was equipped with magnetic stirring bar, cooling bath (liquid nitrogen), stopcock connected to an ammonia cylinder and a vacuum system. The flask was charged with FeCl3 (0.1 g) and evacuated. Ammonium gas was condensed to give liquid ammonium (600 ml). Potassium (19.50 g 0.50 mole) was added in small pieces (each about 0.5 g) under an argon atmosphere. The solution initially became blue but became a grey suspension after heating at reflux for 30 min. Into the potassium amide/liquid ammonia suspension was added in small portions isoquinoline-7-carboxylic acid {ref F. T. Tyson, JACS, 1939, 61,183} (17.0 g 0.10 mole). The free acid initially dissolved but the formed potassium salt soon precipitated as fine particles to give a suspension which was heated at reflux for 6 h. After careful addition of tetraethylethylene diamine (TEEDA) (86 g 0.50 mole), toluene (170 ml) and 18-crown-6 (1 g) the ammonia was allowed to evaporate slowly over 40 h to give a new suspension of the isoquinoline-7-carboxylic acid potassium salt. The reaction mixture was heated to 87° C. for 48 h. A sample was removed and analysed by nmr which indicated that there was still some unreacted starting material present. Ammonia was bubbled through the reaction mixture for 2 h and nmr analysis then revealed that no starting material remained. The reaction was then cooled to −16° C., ice (200 g) was added to destroy excess potassium amide and all solvents evaporated at 76° C. and 7 mmHg and then at 65° C. and 0.7 mmHg to give a powder which was dissolved in water (1.2L) and filtered through Celite to give a clear solution. This was acidified to pH 7 by addition of acetic acid (34 g) and allowed to stand overnight. The precipitate was collected by filtration, washed with water (50 ml×2) and dried by azeotroping with ethanol (50 ml×2) at 50° C. and 7 mmHg then at 50° C. and 0.7 mmHg to give the crude product (17.6 g 94%) as an off-white powder. The crude product (17.6 g) was dissolved in water (4L), and concentrated HCl was added to give a pH of 1.30. The solution was stirred for 1 h, and filtered through Celite to give a clear solution to which was added concentration ammonia solution to give a pH of 5.07. After stirring for 2 h and standing overnight the precipitate was filtered, washed with water (50 ml×2) and dried by azeotroping with ethanol (50 ml×2) at 50° C. and 7 mmHg, and then at 50° C. and 0.7 mmHg to give title compound (15.5 g 88%) as a pale brown solid.

$^1$H nmr (DMSO) 9.20 (1H,s); 8.40 (1H,d); 8.10 (1H,d); 7.85 (1H,d); 7.30 (1H,d).

Example 89

Ethyl 1-aminoisoquinoline-7-carboxylate hydrochloride

To a suspension of 1-aminoisoquinoline-7-carboxylic acid TFA salt (6 g, 20 mmol) in anhydrous ethanol (150 mL) was added thionyl chloride (7.7 mL, 10 eq.) slowly at 0° C. and the reaction mixture was then refluxed for 5 hours. The volatiles were removed under vacuo and the resultant solid treated with diethyl ether and filtered to give the title compound as a brown solid.

1H nmr (D$_2$O) 8.40 (1H,s); 8.05 (1H,d); 7.60 (1H,d); 7.40 (1H,d); 6.95 (1H,d); 4.30 (2H,q); 1.35 (3H,t).

Example 90

Ethyl 1-benzylaminoisoquinoline-7-carboxylate trifluoroacetate

To a suspension of ethyl 1-aminoisoquinolinecarboxylate HCl salt (126 mg, 0.5 mmol), and potassium carbonate (152 mg, 1.1 mmol) in anhydrous DMF was added benzyl bromide (65 μL, 0.55 mmol) and the reaction mixture left to stir at room temperature overnight. Purification by preparative HPLC gave the title compound as a white solid.

$^1$H nmr (CD$_3$OH) 9.05 (1H,s); 8.30 (1H,d); 7.85 (1H,d); 7.55 (1H,d); 7.20 (5H,m); 7.05 (1H,d); 5.35 (2H,s); 4.30 (2H,q); 1.25 (3H,t)

Exanple 91

Ethyl 1-amino-3,4-dihydroisoquinoline-7-carboxylate trifluoroacetate

A vigorously stirred solution of ethyl 1-aminoisoquinoline-7-carboxylate (100 mg, 0.40 mmol) in 50% hydrochloric acid solution (10 ml), containing platinum oxide (20 mg) was treated with hydrogen gas at atmospheric pressure overnight. The reaction mixture was filtered through celite, concentrated and purified by preparative HPLC to yield the title compound as a white solid.

$^1$H nmr (CD$_3$CN) 8. 40 (1H,s); 8.15 (1H,d); 7.45 (1H,d); 4.30 (2H,q); 3.45 (2H,m); 3.05 (2H,m); 1.35 (3H,t).

Example 92

1-Amino-7-hydroxymethylisoquinoline

Ethyl 1-aminoisoquinolinecarboxylate hydrochloride (1 g) was partitioned between ethylacetate and 2M sodium hydroxide solution. The ethylacetate layer was washed with brine, dried over magnesium sulphate, filtered and evaporated to dryness. The residue was dissolved in dry THF (10 ml.), cooled to –5° C. and a 1M solution of diisobutylaluminium hydride (12 mls.) added dropwise. The mixture was stirred at 0° C. for 2 hrs. then at room temperature for a further 2 hrs. Ethyl acetate (50 ml.) and 2M sodium hydroxide solution (5 ml.) were then added. The ethylacetate solution was then separated, washed with brine, dried over magnesium sulphate, filtered and evaporated to give the product as a brown solid.

1H nmr (CD$_3$CN) 7.80 (1H,d); 7.70 (1H,s); 7.60 (1H,d); 7.50 (1H,d); 6.90 (1H,d).

Example 93

1-Amino-7-bromomethylisoquinoline

1-Amino-7-hydroxymethylisoquinoline (0.2 g) was dissolved in dry THF (10 ml.) and phosphorous tribromide (0.03 ml.) added in one portion. A white precipitate was seen to form and the suspension was stirred for 1 hr. at room temperature. The mixture was evaporated to dryness and triturated with diethylether to give the product.

$^1$H nmr (CD$_3$CN) 8.20 (1H,s); 7.80 (1H,d); 7.60 (1H,d); 7.35 (1H,d); 7.00 (1H,d).

Assay Protocols

Enzyme Inhibition Assays

Enzyme assays were carried out at room temperature in 0.1M phosphate buffer, pH7.4 according to the method of Tapparelli et al (J. Biol. Chem. 1993,268,4734–4741). Purified human factor Xa, trypsin, thrombin and plasmin were purchased from Alexis Corporation, Nottingham, UK. Urokinase was purchased from Calbiochem, Nottingham, UK. Chromogenic substrates for these enzymes; pefachrome-FXA, pefachrome-TRY, pefachrome-TH, pefachrome-PL and pefachrome-UK were purchased from Pentapharm AG, Basel, Switzerland. Product (p-nitroaniline) was quantified by adsorption at 405 nm in 96 well microplates using a Dynatech MR5000 reader (Dynex Ltd, Billingshurst, UK). Km and Ki were calculated using SAS PROC NLIN (SAS Institute, Cary, NC, USA, Release 6.11) $K_m$ values were determined as 100.9 μM for factor Xa/pefachrome-FXA and 81.6 μM for trypsin/pefachrome-TRY. Inhibitor stock solutions were prepared at 40 mM in Me2SO and tested at 500 μM, 50 μM and 5 μM. Accuracy of Ki measurements was confirmed by comparison with Ki values of known inhibitors of factor Xa and trypsin.

In agreement with published data, benzamidine inhibited factor Xa, trypsin, thrombin, plasmin and urokinase with Ki values of 155 μM, 21 μM, 330 μM, 200 μM and 100 nM respectively. NAPAP inhibited thrombin with a Ki value of 3 nM. Compounds of the invention were found to have activity in these assays. By way of example the inhibitors described in Example 75 demonstrated a Ki of 8nM and Example 8 demonstrated a Ki of 70 nM when tested against Factor Xa.

Antithrombotic Activity

The test material (Factor Xa inhibitor) was administered either intravenously, intraperitoneally or orally to a group of rats for experiment. A second group received vehicle (saline) only as a control, and a third group of animals received a standard antithrombotic (subcutaneous 1 mw heparin) as a positive control.

To perform the experiment male Sprague-Dawley rats (250–400 g in weight) were anaesthetised by the inhalation of isoflurane with the addition of oxygen and nitrous oxide. The left or right femoral vein was carefully exposed and isolated from the femoral artery and saphenous nerve. Following removal of connective tissue a cannula containing physiological saline was inserted into the femoral vein.

A segment of each of the left and right jugular vein was exposed and separated from the surrounding connective tissue. Each segment consisted of the section of vein between the exit point from the thorax to the vessel's first major junction.

At the desired interval following the administration of the test material or vehicle a bolus injection of 'deactivated' human serum (1.32 ml·kg$^{-1}$) was administered over less than 30 seconds, via the femoral vein cannula. Two minutes following the thrombus challenge both the jugular vein segments were ligatured at both ends and left in situ for thrombi to form.

After 10 min both jugular segments were carefully excised, and placed in a petri dish containing 0.9% saline. A blood sample (1.8 ml blood+0.2 ml3.8% sodium citrate) was obtained by cardiac puncture and the animal sacrificed by an overdose of Expiral (sodium pentobarbitone) administered intravenously via the femoral vein cannula or by cardiac puncture. The 2 segments of jugular vein were carefully dissected longitudinally along one surface to expose the lumen and dispel the vessel contents into the saline. The tissues were examined for the presence of any developed thrombi and scored accordingly.

Thrombus score:
 0=No thrombus
 1=One or several small thrombi
 2=Several larger thrombi
 3=Large thrombus occluding the vessel Compounds of the invention were found to have significant antithrombotic activity in these assays.

Partial Thromboplastin Time Test Protocol

Venous blood was collected into 3.2% (0.109 m) trisodium citrate vacutainer tubes at 1 volume of anticoagulant to nine volumes of blood.

The blood cells were separated by centrifugation at 700 g for ten minutes to yield plasma, which was frozen at 70° C. until required.

To perform the test, 100 µl of plasma was pipetted into in a glass test tube, 1 µl of test compound in DMSO was added, and allowed to warm to 37° over two minutes.

100 µl of warm (37°) Manchester (tissue thromboplastin) reagent (Helena Biosciences, UK) was added, allowed to equilibrate for sixty seconds.

100 µl of warm (37°) 25 mM calcium chloride solution was added to initiate clotting.

The test tube was tilted three times through a 90° angle every five seconds to mix the reagents and the time to clot formation recorded.

Data from a series of observations and test compound concentrations are analysed by a SAS statistical analysis program and a CT2 (Concentration required to double clotting time) for each compound is generated.

Compounds of the invention were found to significantly elongate the partial thromboplastin time.

What is claimed is:

1. A serine protease inhibitor compound of formula I

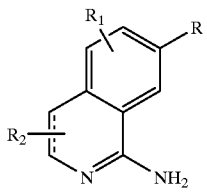

(I)

where $R_1$ is hydrogen, halo, cyano, nitro, hydroxyl, amino, alkoxy, alkyl, aminoalkyl, hydroxyalkyl, thiol, alkylthio, aminosulphonyl, alkoxyalkyl, alkoxycarbonyl, acyloxymethoxycarbonyl or alkylamino optionally substituted by hydroxy, alkylamino, alkoxy, oxo, aryl, cycloalkyl, amino, halo, cyano, nitro, thiol, alkylthio, alkylsulphonyl, alkylsulphenyl, alkylsulphonamido, alkylaminosulphonyl, haloalkoxy and haloalkyl;

$R_2$ is hydrogen, halo, methyl, amino, hydroxy or oxo; and

R is X—X—Y($R_7$)—L—Lp(D)n wherein each X independently is a C, N, O or S atom or a CO, $CR_1$, C $(R_1)_2$ or $NR_1$ group, at least one X being C, CO, $CR_1$ or a $C(R_1)_2$ group;

Y (the α-atom) is a nitrogen atom or a $CR_1$ group or Y and L taken together form a cyclic group;

$R_7$ is a lipophilic group selected from alkyl, alkenyl, mono- or bi-cycloalkyl, aryl, heteroaryl, mono- or bicycloalkylalkyl, mono- or bicycloalkylalkenyl, aralkyl, heteroaryl-alkyl, arylalkenyl, heteroarylalkenyl all optionally substituted by a group $R_1$;

L is an organic linker group containing 1 to 5 backbone atoms selected from C, N, O and S, or a branched alkyl or cyclic group;

Lp is a lipophilic organic group selected from alkyl, heterocyclic, alkenyl, alkaryl, cycloalkyl, polycycloalkyl, cycloalkenyl, aryl, aralkyl or haloalkyl group or a combination of two or more such groups optionally substituted by one or more of oxa, thia, aza or $R_1$ groups;

D is a hydrogen bond donor group; and n is 0, 1 or 2;

or a physiologically tolerable salt thereof.

2. A compound as claimed in claim 1 wherein the double bond is present between the 3 and 4 positions of the fused ring.

3. A compound as claimed in claim 1, wherein $R_1$ represents hydrogen, hydroxy, amino or alkyl.

4. A compound as claimed in claim 1, wherein $R_1$ is on the 6-position of the fused ring.

5. A compound as claimed in claim 1, wherein $R_2$ is hydrogen.

6. A compound as claimed in claim 1, wherein the linker X—X is —CH=CH—, —CONH—, —CONR$_1$—, —NH—CO—, —NH—CH$_2$—, —CH$_2$—NH—, —CH$_2$O—, —OCH$_2$—, —COO—, —OC=O— or —CH$_2$CH$_2$—.

7. A compound as claimed in claim 6 wherein the X moiety nearest Y is NH.

8. A compound as claimed in claim 6, wherein the X moiety nearest the fused ring is CH$_2$ or CO.

9. A compound as claimed in claim 6 wherein X—X is —CONH—.

10. A compound as claimed in claim 1, wherein Y is CH.

11. A compound as claimed in claim 1, wherein $R_7$ represents an unsubstituted or $R_1$-substituted aryl, heteroaryl or cyclohexyl group.

12. A compound as claimed in claim 11 wherein $R_7$ represents phenyl or naphthyl.

13. A compound as claimed in claim 1, wherein the linker L represents CO, CH$_2$NH, CONR$_1$ (CH$_2$)$_m$, (CH$_2$)$_m$N (R$_1$) CO (CH$_2$)$_m$, (CH$_2$)$_{m+2}$, (CH$_2$)$_m$CO (CH$_2$)$_m$, (CH$_2$)$_m$OC=O, (CH$_2$)$_m$O or CH=CH(CH$_2$)$_m$ (where each m is independently 0 or 1).

14. A compound as claimed in claim 13 wherein the linker L represents CONR$_1$(CH$_2$)$_m$, CO or (CH$_2$)NR$_1$CO where m is 0 or 1.

15. A compound as claimed in claim 1, wherein Lp is a cycloalkyl, azacycloalkyl, diazacycloalkyl, phenyl, naphthyl, adamantyl, decalinyl, tetrahydrodecalinyl, bicycloalkyl, mono- or diazabicycloalkyl, mono- or bicycloheteroaromatic or a linear or branched alkyl, alkylene, alkenyl or alkenylene group all optionally substituted by oxa, aza, thia or one or more groups $R_1$, or a combination of at least two such groups linked by a spiro linkage or a single or double bond or by C=O, O, S, SO$_2$, CONR$_1$, NR$_1$—CO—, NR$_1$ linkage.

16. A compound as claimed in claim 15, wherein Lp is a methylcyclohexyl, methylcyclohexylmethyl, methylphenylmethyl, phenylethyl, benzylpiperidinyl, benzoylpiperidinyl, bispiperidinyl or phenylpiperazinyl.

17. A compound as claimed in claim 1, wherein D is attached to Lp.

18. A compound as claimed in claim 17, wherein D contains a hydrogen bond donor atom selected from nitrogen and oxygen.

19. A compound as claimed in claim 18, wherein D is formed from a hydroxyl group, a primary, secondary or tertiary amine, or a primary or secondary imine group as part of an amidine or guanidine or a saturated or unsaturated heterocyclic group containing 5 to 7 ring atoms and having a ring nitrogen.

20. A compound as claimed in claim 1, wherein Y is carbon and has the conformation that would result from construction from a D-α-aminoacid NH$_2$—CR$_1$(R$_7$)—COOH.

21. A pharmaceutical composition comprising a serine protease inhibitor as claimed in claim 1 together with at least one pharmaceutically acceptable carrier or excipient.

22. A method of treatment of the human or non-human animal body to combat a condition responsive to a serine protease inhibitor, said method comprising administering to said body an effective amount of a serine protease inhibitor as claimed in claim 1.

23. A compound which is selected from 1-Aminoisoquinolin-7-oyl-D-phenylglycinyl-D-2-naphthylalaninylproline, 1-aminoisoquinolin-7-oyl-D-phenylglycine-4-(4'-pyridyl) piperidinamide, 1-Aminoisoquinolin-7-oyl-D-phenylglycine-4-methoxybenzylamide, 1-Aminoisoquinolin-7-oyl-D-phenylglycine-4-(4'-hydroxyphenyl) piperazinamide, 1-Aminoisoquinolin-7-oyl-D-phenylglycine-4-(2,4-difluorophenyl) piperazinamide, 1-Aminoisoquinolin-7-oyl-D-cyclohexylglycine-4-(4'-pyridyl) piperazinamide, 1-Aminoisoquinolin-7-oyl-D,L-1-naphthylglycine-4,4-bipiperidinamide, 2(R)-{[N-(1-Aminoisoquinoline)-7-oyl]amino}-2-phenylethyl-4-methylbenzamide and 1-Aminoisoquinolin-7-oyl-D-phenylglycine-4,4'-(1-methyl) bipiperidinamide.

24. A compound which is selected from 1-amino-7-carbonyl-isoquinolines and 3,4-dihydro-1-amino-7-carbonyl-isoquinolines.

25. A compound as claimed in claim 24 having an amino-carbonyl substituent at the 7-position.

26. A compound as claimed in claim 24, having an amino group at the 6-position.

27. A compound which is selected from 1-aminoisoquinoline-7-carboxylic acids and salts, esters and amides thereof.

28. A compound as claimed in claim 27 having an amino group at the 6-position.

* * * * *